US012653375B2

(12) United States Patent　　(10) Patent No.:　US 12,653,375 B2
Iwane　　(45) Date of Patent:　Jun. 16, 2026

(54) MEDICAL IMAGE PROCESSING DEVICE, ENDOSCOPE SYSTEM, AND OPERATION METHOD OF MEDICAL IMAGE PROCESSING DEVICE

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 56 days.

(21) Appl. No.: 18/537,762

(22) Filed: Dec. 12, 2023

(65) Prior Publication Data

US 2024/0108198 A1　Apr. 4, 2024

Related U.S. Application Data

(63) Continuation of application No. PCT/JP2022/018434, filed on Apr. 21, 2022.

(30) Foreign Application Priority Data

Jun. 16, 2021　(JP) ................................. 2021-100526

(51) Int. Cl.
　*A61B 1/00*　　(2006.01)
　*G06T 5/70*　　(2024.01)
　　　(Continued)

(52) U.S. Cl.
　CPC .......... *A61B 1/000095* (2022.02); *G06T 5/70* (2024.01); *G06T 7/11* (2017.01);
　　　(Continued)

(58) Field of Classification Search
　None
　See application file for complete search history.

(56) References Cited

U.S. PATENT DOCUMENTS 5,107,838 A * 4/1992 Yamaguchi .......... A61B 5/0263
　　　　　　　　　　　　　600/526
5,615,324 A　　3/1997 Kuboyama
　　　　　　(Continued)

FOREIGN PATENT DOCUMENTS

CN　　103249349　　8/2013
CN　　109381152　　2/2019
　　　　(Continued)

OTHER PUBLICATIONS

"International Search Report (Form PCT/ISA/210) of PCT/JP2022/018434", mailed on Jul. 26, 2022, with English translation thereof, pp. 1-5.

(Continued)

*Primary Examiner* — Martin Mushambo
(74) *Attorney, Agent, or Firm* — JCIPRNET

(57)　　　ABSTRACT

A medical image processing device sets a boundary line, which indicates a boundary between a region of interest and a region of disinterest in a subject, in a still image of an endoscopic image, generates a boundary line display image in which the boundary line is displayed on the still image, and performs a control of displaying a video image of the endoscopic image and the boundary line display image on a display device. The boundary line to be displayed on the boundary line display image is displayed by being updated for each setting of the boundary line.

18 Claims, 25 Drawing Sheets

(51) Int. Cl.
  *G06T 7/00* (2017.01)
  *G06T 7/11* (2017.01)
  *G06T 11/23* (2026.01)

(52) U.S. Cl.
  CPC .... *G06T 11/23* (2026.01); *G06T 2207/10016* (2013.01); *G06T 2207/10068* (2013.01); *G06T 2207/20104* (2013.01); *G06T 2207/30096* (2013.01); *G06T 2210/41* (2013.01)

(56) References Cited

U.S. PATENT DOCUMENTS

| | | | | |
|---|---|---|---|---|
| 6,385,476 | B1 * | 5/2002 | Osadchy | A61B 5/283 378/68 |
| 9,412,054 | B1 * | 8/2016 | Krupnik | A61B 1/041 |
| 2001/0007468 | A1 * | 7/2001 | Sugimoto | H04N 7/181 348/E7.086 |
| 2005/0209507 | A1 * | 9/2005 | Suzuki | A61L 2/26 600/101 |
| 2008/0008369 | A1 * | 1/2008 | Koptenko | G06T 7/12 382/199 |
| 2008/0247619 | A1 | 10/2008 | Li | |
| 2010/0119110 | A1 * | 5/2010 | Kanda | G06F 18/21 382/128 |
| 2013/0258080 | A1 | 10/2013 | Kuriyama | |
| 2018/0042468 | A1 * | 2/2018 | Teramura | H04N 23/74 |
| 2019/0043188 | A1 * | 2/2019 | Wang | G06T 7/62 |
| 2019/0223704 | A1 * | 7/2019 | Chen | A61B 1/045 |
| 2019/0247130 | A1 * | 8/2019 | State | A61B 34/20 |
| 2019/0272652 | A1 * | 9/2019 | Mak | A61B 5/7445 |
| 2020/0022560 | A1 * | 1/2020 | Oosake | A61B 1/0684 |
| 2020/0345225 | A1 | 11/2020 | Iwane | |
| 2021/0000327 | A1 * | 1/2021 | Kitamura | A61B 1/000094 |
| 2021/0233298 | A1 | 7/2021 | Usuda | |
| 2022/0076458 | A1 | 3/2022 | Shigeta | |
| 2023/0419517 | A1 * | 12/2023 | Nakamura | G06T 7/62 |
| 2024/0320877 | A1 | 9/2024 | Shigeta | |

FOREIGN PATENT DOCUMENTS

| | | | |
|---|---|---|---|
| CN | 111683583 | 9/2020 | |
| CN | 112969404 | 6/2021 | |
| JP | H07262371 | 10/1995 | |
| JP | 2001137206 | 5/2001 | |
| JP | 2021037036 | 3/2021 | |
| JP | 2021037036 | A * | 3/2021 |
| JP | 7122328 | B2 * | 8/2022 |
| WO | 2020075254 | 4/2020 | |
| WO | 2020235502 | 11/2020 | |

OTHER PUBLICATIONS

"Written Opinion of the International Searching Authority (Form PCT/ISA/237) of PCT/ JP2022/018434", mailed on Jul. 26, 2022, with English translation thereof, pp. 1-8.
"Search Report of Europe Counterpart Application", issued on Sep. 17, 2024, p. 1-p. 7.
"Notice of Reasons for Refusal of Japan Counterpart Application", issued on Mar. 10, 2026, with English translation thereof, p. 1-p. 9.
"Office Action of European Counterpart Application", issued on Apr. 9, 2026, p. 1-p. 7.
"The First Office Action of China Counterpart Application", issued on Apr. 13, 2026, with English translation thereof, p. 1-p. 17.

* cited by examiner

73

BOUNDARY LINE GENERATION UNIT

BOUNDARY LINE DETECTION SECTION — 101

DRAWING DETECTION SECTION — 102

POSITIVE POINT/NEGATIVE POINT ANALYSIS SECTION — 103

101

19

111

LEARNING MODEL

18

74

BOUNDARY LINE CORRECTION UNIT

ANOMALY DEGREE DETERMINATION SECTION —142

(A)                                        (B)

10 — ENDOSCOPE SYSTEM

610 — DIAGNOSIS SUPPORT APPARATUS

640 — MEDICAL IMAGE PROCESSING UNIT DEVICE

22 — PACS

621 — FIRST EXAMINATION DEVICE

622 — SECOND EXAMINATION DEVICE

· · ·

623 — NTH EXAMINATION DEVICE

NETWORK — 626

630 — MEDICAL SERVICE SUPPORT APPARATUS

640 — MEDICAL IMAGE PROCESSING UNIT DEVICE

MEDICAL IMAGE PROCESSING DEVICE, ENDOSCOPE SYSTEM, AND OPERATION METHOD OF MEDICAL IMAGE PROCESSING DEVICE

CROSS-REFERENCE TO RELATED APPLICATIONS

This application is a Continuation of PCT International Application No. PCT/JP2022/018434 filed on 21 Apr. 2022, which claims priority under 35 U.S.C § 119(a) to Japanese Patent Application No. 2021-100526 filed on 16 Jun. 2021. The above application is hereby expressly incorporated by reference, in its entirety, into the present application.

BACKGROUND OF THE INVENTION

1. Field of the Invention

The present invention relates to a medical image processing device, an endoscope system, and an operation method of a medical image processing device.

2. Description of the Related Art

In recent years, a computer-aided diagnosis (CAD) technique for discriminating a lesion by performing appropriate image processing on an endoscopic image has been put into practical use, and information for supporting a diagnosis is provided to a user. For example, it is possible to show a range of the lesion, which is obtained through the CAD, in the endoscopic image.

There is known a medical image processing device that issues a notification of a region of interest using a figure without obstructing the observation of a boundary between the region of interest and a region of disinterest in a case of showing a range of a lesion, which is obtained through CAD, in an endoscopic image (WO2020/075254A1).

SUMMARY OF THE INVENTION

In a case where a region of interest is a lesion, a resection range is set by identifying a boundary line (demarcation line) of the lesion in endoscopic submucosal dissection (ESD) or endoscopic mucosal resection (EMR). For example, in a method of determining a range of the lesion for each frame, which is a unit of imaging, a range to be displayed as the lesion also changes with the change in time. Therefore, the boundary line of the lesion changes moment by moment on a video, which may make it difficult to determine a correct range of the lesion, that is, the boundary line of the lesion, with high accuracy.

An object of the present invention is to provide a medical image processing device, an endoscope system, and an operation method of a medical image processing device for providing information on a boundary between a region of interest and a region of disinterest with higher accuracy.

According to an aspect of the present invention, there is provided a medical image processing device comprising: a processor, in which the processor is configured to: acquire an endoscopic image obtained by imaging a subject with an endoscope; set a boundary line, which indicates a boundary between a region of interest and a region of disinterest in the subject, in a still image of the endoscopic image; generate a boundary line display image in which the set boundary line is displayed on the still image; and perform a control of displaying a video image of the endoscopic image and the boundary line display image on a display device, and the boundary line to be displayed on the boundary line display image is displayed by being updated for each setting of the boundary line.

It is preferable that the processor is configured to detect and set the boundary line based on the still image.

It is preferable that the display device includes a first display device and a second display device, and that the processor is configured to perform a control of displaying the still image and/or the boundary line display image on the first display device and/or the second display device that is provided in a small terminal connected to the medical image processing device.

It is preferable that the processor is configured to, in a case of displaying the still image, set the boundary line based on a drawing generated by a user on the displayed still image.

It is preferable that the drawing is subjected to smoothing processing.

It is preferable that the drawing is a positive point generated in the region of interest of the still image through a determination of the user.

It is preferable that the drawing is a negative point generated in the region of disinterest of the still image through a determination of the user.

It is preferable that the processor is configured to perform a control of displaying the still image on the second display device, and that the drawing is the drawing generated on the still image displayed on the second display device.

It is preferable that the processor is configured to newly set the boundary line obtained by correcting the boundary line displayed on the boundary line display image as the boundary line.

It is preferable that the processor is configured to perform a control of displaying the boundary line display image on the second display device.

It is preferable that the processor is configured to perform a control of displaying the video image on a main screen of the first display device and displaying the boundary line display image on a sub screen of the first display device.

It is preferable that the processor is configured to perform a control of displaying the still image on a sub screen of the first display device.

It is preferable that the processor is configured to display the boundary line on the video image corresponding to the boundary line displayed on the boundary line display image.

It is preferable that the processor is configured to control whether or not to display the boundary line on the video image based on a user's instruction or the endoscopic image.

It is preferable that the processor is configured to end update of the boundary line based on a user's instruction or the endoscopic image.

It is preferable that the still image is acquired in the same examination as the video image or is acquired in an examination different from the video image.

In addition, according to another aspect of the present invention, there is provided an endoscope system comprising: an endoscope that images the subject; the display device; and the medical image processing device.

It is preferable that the display device includes a first display device and a second display device.

Further, according to still another aspect of the present invention, there is provided an operation method of a medical image processing device, comprising: a step of acquiring an endoscopic image obtained by imaging a subject with an endoscope; a step of setting a boundary line, which indicates a boundary between a region of interest and a region of disinterest in the subject, in a still image of the endoscopic image; a step of generating a boundary line display image in which the set boundary line is displayed on the still image; and a step of performing a control of displaying a video image of the endoscopic image and the boundary line display image on a display device, in which the boundary line to be displayed on the boundary line display image is displayed by being updated for each setting of the boundary line.

According to the aspects of the present invention, it is possible to provide information on the boundary between the region of interest and the region of disinterest with higher accuracy.

DESCRIPTION OF THE PREFERRED EMBODIMENTS

Figure 1:
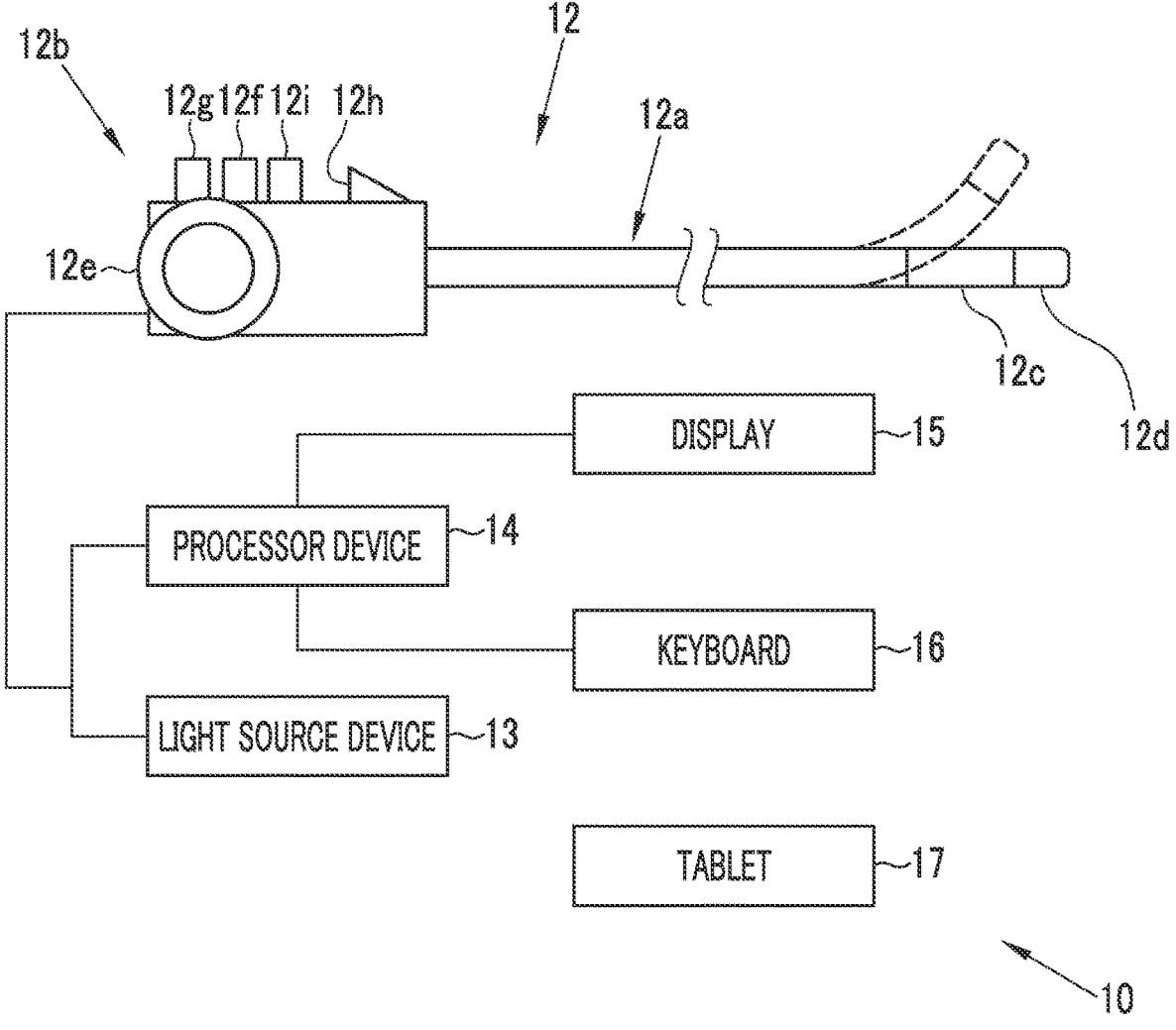
FIG. 1 is an external view of an endoscope system.

As shown in FIG. 1, an endoscope system 10 includes an endoscope 12, a light source device 13, a processor device 14, a display 15 which is a first display device, a keyboard 16, and a tablet 17 which is a small terminal provided in a second display device. It is preferable that the second display device is a touch panel. The display device includes the first display device and the second display device and is used to represent a case where these are not distinguished from each other. The endoscope 12 is optically connected to the light source device 13 and is electrically connected to the processor device 14. The processor device 14 is provided with a function as a medical image processing device. The tablet 17 is connected to the processor device 14 through wireless or wired connection.

In the present embodiment, the medical image is an endoscopic image. The endoscopic image is an image obtained by imaging an observation target of an endoscope, which is a subject, with the endoscope. In addition, in the present embodiment, the processor device 14 is provided with the function as the medical image processing device, but a device that performs the function of the medical image processing device may be configured as a device separate from the processor device 14. Further, various connections are not limited to wired connections, and may be wireless connection or may be connection via a network. Therefore, the function of the medical image processing device may be performed by an external device connected via the network.

The endoscope 12 includes an insertion part 12a to be inserted into a body of a subject under examination having an observation target, an operation part 12b provided at a proximal end portion of the insertion part 12a, and a bending portion 12c and a distal end portion 12d provided on a distal end side of the insertion part 12a. By operating an angle knob 12e (see FIG. 1) of the operation part 12b, the bending portion 12c performs a bending movement. The distal end portion 12d is directed in a desired direction by the bending movement of the bending portion 12c. A forceps channel (not shown) for inserting a treatment tool or the like is provided from the insertion part 12a to the distal end portion 12d. The treatment tool is inserted into the forceps channel through a forceps port 12h. Further, air supply, water supply, or suction is also performed through the forceps port 12h.

The operation part 12b includes, in addition to the angle knob 12e, a zoom operation portion 12f for changing an imaging magnification, a mode selector switch 12g used for a switching operation of an observation mode, and a freeze switch 12i for acquiring a still image. The switching operation of the observation mode, the zoom operation, or a still image acquisition operation may be an operation or an instruction using the keyboard 16, a foot-switch (not shown), or the like in addition to the mode selector switch 12g, the zoom operation portion 12f, or the freeze switch.

The endoscope system 10 comprises a normal observation mode and a special observation mode. In the normal observation mode, a normal image, which is a natural color-tone endoscopic image obtained by imaging the observation target using white light as illumination light, is displayed on the display 15. In the special observation mode, a special image, which is an endoscopic image obtained by imaging the observation target irradiated with illumination light having a specific spectrum different from that of white light, is displayed on the display 15. An observation support mode can be added to each of the normal observation mode and the special observation mode. In the observation support mode, a function of displaying on the display device a video image of the endoscopic image and a boundary line display image in which a boundary line, which indicates a boundary between a region of interest and a region of disinterest, is displayed on the still image of the endoscopic image is performed.

Figure 2:
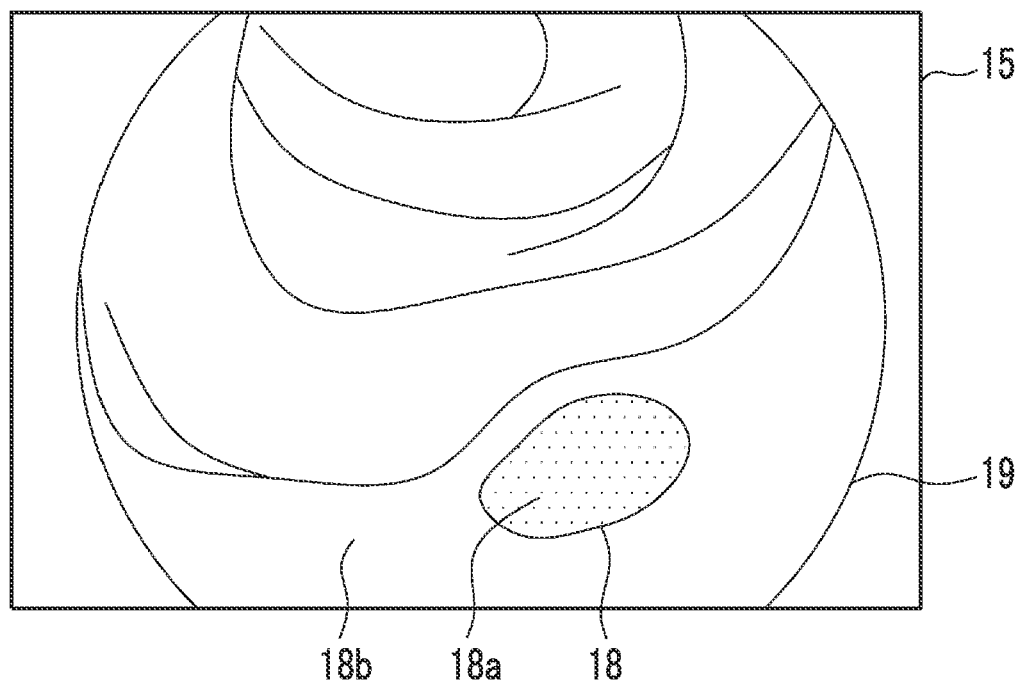
FIG. 2 is an image diagram showing a boundary line.

As shown in FIG. 2, a boundary line 18 is, for example, a line indicating a boundary between a lesion region 18a, which is the region of interest, and a non-lesion region 18b, which is the region of disinterest, in a still image 19 of the endoscopic image obtained by imaging a stomach. The boundary line 18 is a normally closed curve, and it is important to accurately understand the boundary line 18 in order to identify the boundary line 18 and set a resection line or a resection range in ESD or EMR. In the diagram, the lesion region 18a is indicated by hatching.

The normal image or the special image is used as the endoscopic image used in the observation support mode. The observation mode may be provided with a multi-observation mode or the like in which the normal image and the special image are automatically switched and acquired. In the multi-observation mode, the observation support mode can also be added, and the normal image and the special image can also be automatically switched and acquired in a case where the observation support mode is added.

The processor device 14 is electrically connected to the display 15 and the keyboard 16. The display 15 displays, for example, the video image of the endoscopic image acquired during an examination, the still image 19, a boundary line display image, which will be described below, and/or various types of information. The keyboard 16 functions as a user interface for accepting an input operation, such as function settings. An external storage (not shown) for storing images, image information, and the like may be connected to the processor device 14.

Figure 3:
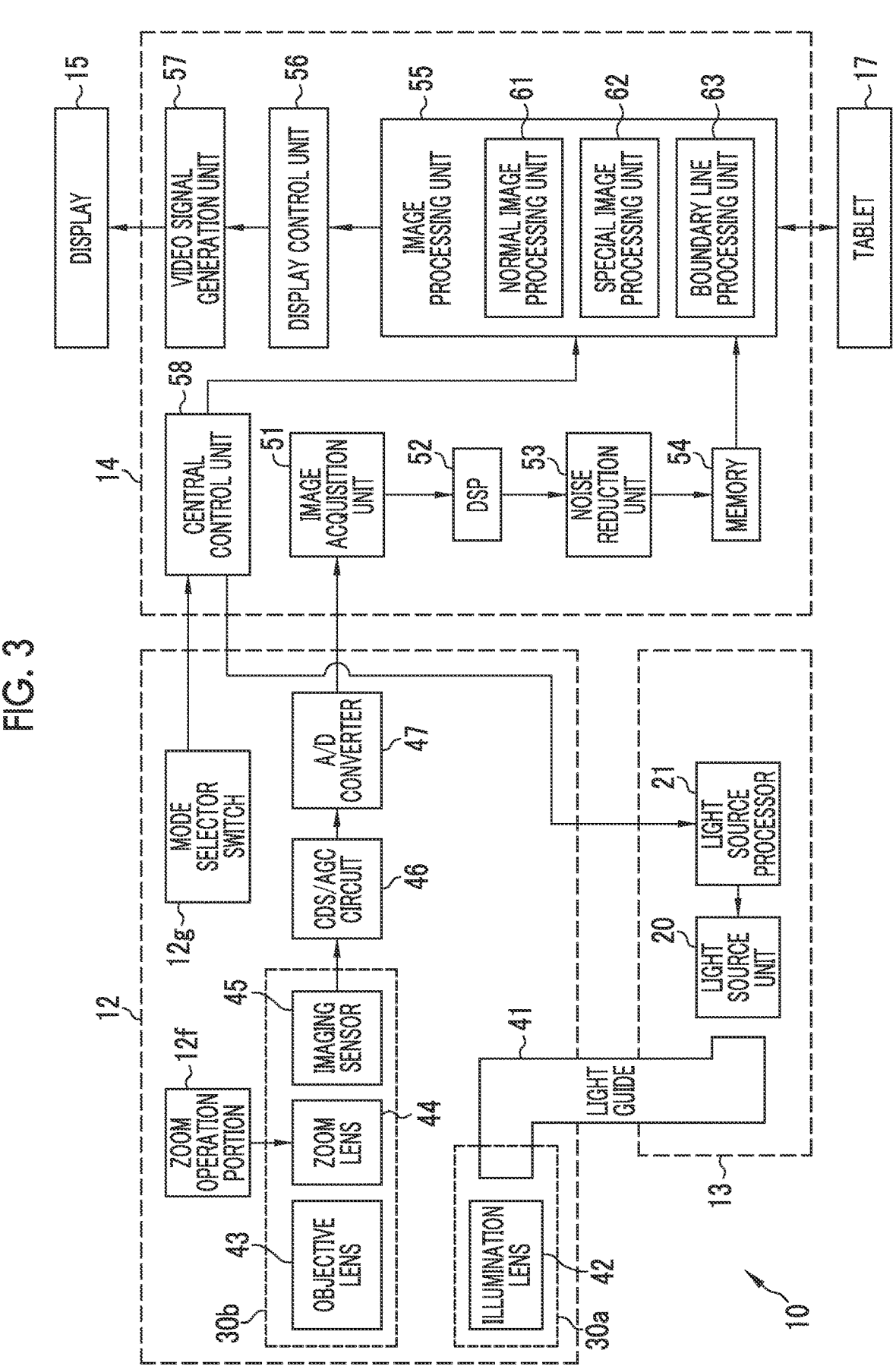
FIG. 3 is a block diagram showing a function of the endoscope system.

As shown in FIG. 3, the light source device 13 emits illumination light to be emitted to the observation target and comprises a light source unit 20 and a light source processor 21 that controls the light source unit 20. The light source unit 20 is composed of, for example, a semiconductor light source such as multi-color light emitting diodes (LEDs), a combination of a laser diode and a phosphor, or a xenon lamp or a halogen light source. Additionally, the light source unit 20 includes, for example, an optical filter for adjusting the wavelength range of light emitted by the LED or the like. The light source processor 21 controls the amount of illumination light by turning on/off each LED or the like or adjusting a drive current and a drive voltage of each LED or the like. Further, the light source processor 21 controls the wavelength range of illumination light by changing the optical filter or the like.

Figure 4:
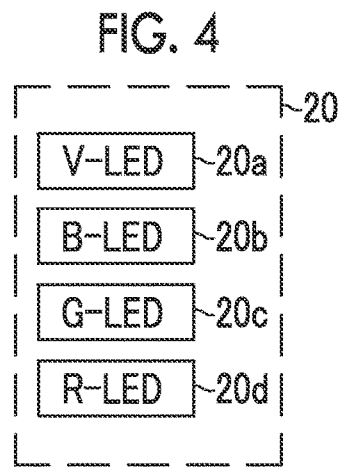
FIG. 4 is an explanatory diagram illustrating four-color LEDs provided in a light source unit.

As shown in FIG. 4, in the present embodiment, the light source unit 20 includes four-color LEDs: a violet light emitting diode (V-LED) 20a; a blue light emitting diode (B-LED) 20b; a green light emitting diode (G-LED) 20c; and a red light emitting diode (R-LED) 20d.

Figure 5:
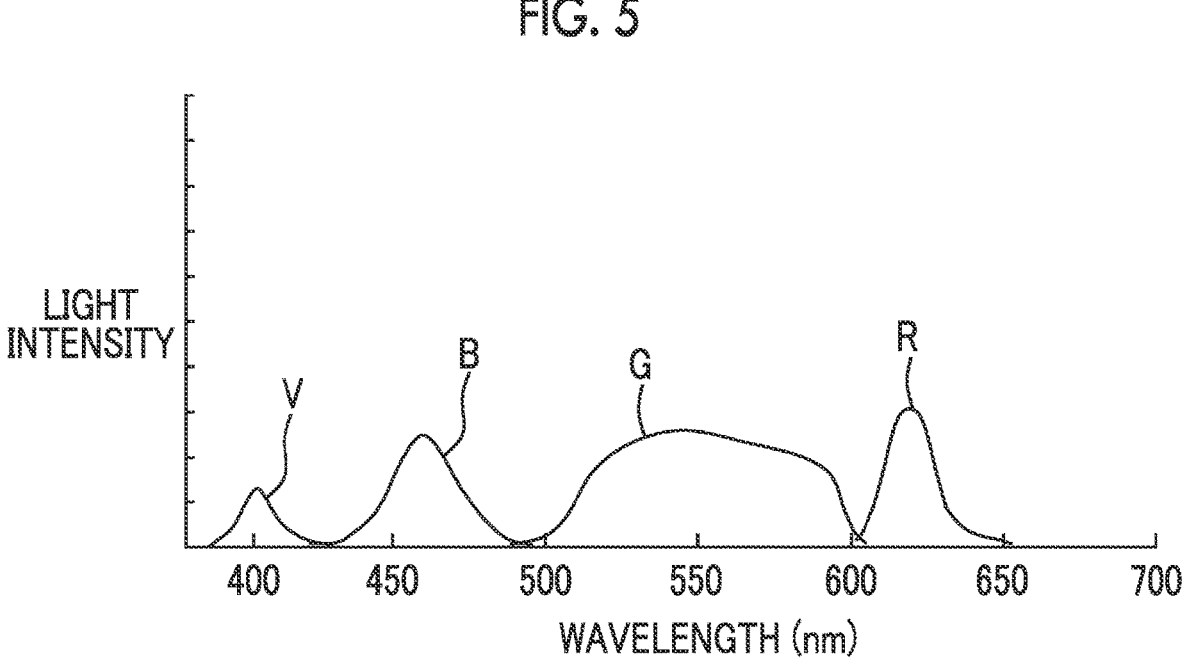
FIG. 5 is a graph showing spectra of violet light V, blue light B, green light G, and red light R.

As shown in FIG. 5, the V-LED 20a generates violet light V with a central wavelength of 410±10 nm and a wavelength range of 380 to 420 nm. The B-LED 20b generates blue light B with a central wavelength of 450±10 nm and a wavelength range of 420 to 500 nm. The G-LED 20c generates green light G with a wavelength range of 480 to 600 nm. The R-LED 20d generates red light R with a central wavelength of 620 to 630 nm and a wavelength range of 600 to 650 nm.

The light source processor 21 controls the V-LED 20a, the B-LED 20b, the G-LED 20c, and the R-LED 20d. The light source processor 21 controls the respective LEDs 20a to 20d to emit normal light of which the combination of light intensity ratios between the violet light V, the blue light B, the green light G, and the red light R is Vc:Bc:Gc:Rc during the normal observation mode.

The light source processor 21 emits illumination light with a specific spectrum by changing, for example, the combination of the light intensity ratios between the violet light V, the blue light B, the green light G, and the red light R in a case where the special observation mode is set.

The light emitted from each of the LEDs 20a to 20d is incident on a light guide 41 via an optical path coupling portion (not shown) composed of a mirror, a lens, or the like. The light guide 41 is incorporated into the endoscope 12 and a universal cord (a cord connecting the endoscope 12 to the light source device 13 and the processor device 14). The light guide 41 propagates light from the optical path coupling portion to the distal end portion 12d of the endoscope 12.

An illumination optical system 30a and an imaging optical system 30b are provided in the distal end portion 12d of the endoscope 12. The illumination optical system 30a includes an illumination lens 42, and the illumination light propagated by the light guide 41 is emitted to the observation target via the illumination lens 42. The imaging optical system 30b includes an objective lens 43, a zoom lens 44, and the imaging sensor 45. Various types of light such as reflected light, scattered light, and fluorescence from the observation target are incident on the imaging sensor 45 via the objective lens 43 and the zoom lens 44. As a result, an image of the observation target is formed on the imaging sensor 45. The zoom lens 44 is freely moved between a telephoto end and a wide end by operating the zoom operation portion 12f, thereby magnifying and reducing the observation target of which the image is formed on the imaging sensor 45.

The imaging sensor 45 is a color imaging sensor provided with any of a red (R) color filter, a green (G) color filter, or a blue (B) color filter for each pixel, and images the observation target and outputs image signals for respective RGB colors. A charge coupled device (CCD) imaging sensor or a complementary metal-oxide semiconductor (CMOS) imaging sensor can be utilized as the imaging sensor 45. Alternatively, instead of the imaging sensor 45 provided with primary color filters, a complementary color imaging sensor provided with complementary color filters, that is, cyan (C), magenta (M), yellow (Y), and green (G), may also be used. In a case where the complementary color imaging sensor is used, four-color image signals, that is, CMYG, are output. Therefore, through complementary-primary color conversion, by converting the four-color image signals, that is, CMYG, into three-color image signals, that is, RGB, it is possible to obtain the same RGB image signals as those of the imaging sensor 45. Alternatively, instead of the imaging sensor 45, a monochrome imaging sensor that is not provided with the color filters may be used.

The imaging sensor 45 is driven and controlled by an imaging control unit (not shown). The central control unit 58 (see FIG. 3) controls the light emission of the light source unit 20 through the light source processor 21 in synchronization with the imaging control unit to perform a control such that the observation target illuminated with the normal light is imaged in the normal observation mode. As a result, a Bc image signal is output from a B pixel of the imaging sensor 45, a Gc image signal is output from a G pixel, and an Rc image signal is output from an R pixel.

A correlated double sampling/automatic gain control (CDS/AGC) circuit 46 performs correlated double sampling (CDS) or automatic gain control (AGC) on an analog image signal obtained from the imaging sensor 45. The image signal that has passed through the CDS/AGC circuit 46 is converted into a digital image signal by an analog/digital (A/D) converter 47. The digital image signal after the A/D conversion is input to the processor device 14.

In the processor device 14, a program related to processing such as image processing is stored in a program memory (not shown). In the processor device 14, the program within the program memory is operated by the central control unit 58 composed of an image processor, which is a first processor, or the like, whereby the functions of an image acquisition unit 51, a digital signal processor (DSP) 52, a noise reduction unit 53, a memory 54, an image processing unit 55, a display control unit 56, a video signal generation unit 57, and the central control unit 58 are realized. Additionally, the central control unit 58 receives information from the endoscope 12 and the light source device 13, and controls each unit of the processor device 14 and controls the endoscope 12 or the light source device 13, based on the received information. Further, information, such as an instruction through the keyboard 16, is also received.

The image acquisition unit 51 acquires the digital image signal of the endoscopic image, which is input from the endoscope 12. The image acquisition unit 51 acquires, for each frame, the image signal obtained by imaging the observation target illuminated with each illumination light. The image acquisition unit 51 may acquire endoscopic images obtained by imaging the observation target illuminated with rays of illumination light having predetermined and different spectra.

The acquired image signal is transmitted to the DSP 52. The DSP 52 performs digital signal processing, such as color correction processing, on the received image signal. The noise reduction unit 53 performs noise reduction processing through, for example, a moving average method or a median filtering method, on the image signal on which the color correction processing or the like has been performed by the DSP 52. The noise-reduced image signal is stored in the memory 54.

The image processing unit 55 acquires the noise-reduced image signal from the memory 54. Then, signal processing, such as color conversion processing, color enhancement processing, and structure enhancement processing, is performed as necessary on the acquired image signal, and a color endoscopic image showing the observation target is generated. The image processing unit 55 comprises a normal image processing unit 61, a special image processing unit 62, and a boundary line processing unit 63.

In the image processing unit 55, the normal image processing unit 61 performs image processing for the normal image, such as the color conversion processing, the color enhancement processing, and the structure enhancement processing, on the input noise-reduced image signal for the normal image for one frame, in the normal observation mode or the observation support mode. The image signal that has been subjected to the image processing for the normal image is input to the display control unit 56.

In the special observation mode, the special image processing unit 62 performs image processing for the special image, such as the color conversion processing, the color enhancement processing, and the structure enhancement processing, on the input noise-reduced image signal for the special image for one frame. The image signal that has been subjected to the image processing for the special image is input as the special image to the display control unit 56.

Since the endoscopic image generated by the image processing unit 55 is the normal image in a case where the observation mode is the normal observation mode, and is the special image in a case where the observation mode is the special observation mode, and the contents of the color conversion processing, the color enhancement processing, and the structure enhancement processing differ depending on the observation modes. In a case of the normal observation mode, the image processing unit 55 generates the normal image by performing the above various types of signal processing of making the observation target have a natural color tone. In a case of the special observation mode, for example, the image processing unit 55 generates the special image by performing the above various types of signal processing of enhancing blood vessels as the observation target.

The display control unit 56 receives the endoscopic image generated by the image processing unit 55 and performs a control to display the endoscopic image on the display 15 in accordance with the control of the central control unit 58. The endoscopic image controlled to be displayed by the display control unit 56 is generated as a video signal to be displayed on the display 15 by the video signal generation unit 57 and is sent to the display 15. The display 15 displays the endoscopic image sent from the video signal generation unit 57 in accordance with the control of the display control unit 56.

The boundary line processing unit 63 functions in the observation support mode. Therefore, the boundary line processing unit 63 operates in conjunction with either the normal image processing unit 61 or the special image processing unit 62. In the observation support mode, the boundary line processing unit 63 acquires the endoscopic image from the memory 54 and sets the boundary line 18, which indicates the boundary between the region of interest and the region of disinterest in the subject, in the still image 19 of the endoscopic image. Then, the boundary line display image in which the set boundary line 18 is displayed on the still image 19 is created, and a control of displaying the boundary line display image and the video image of the endoscopic image on the display device such as the display 15 is performed. The boundary line 18 to be displayed on the boundary line display image is displayed by being updated for each setting of the boundary line 18.

Figure 6:
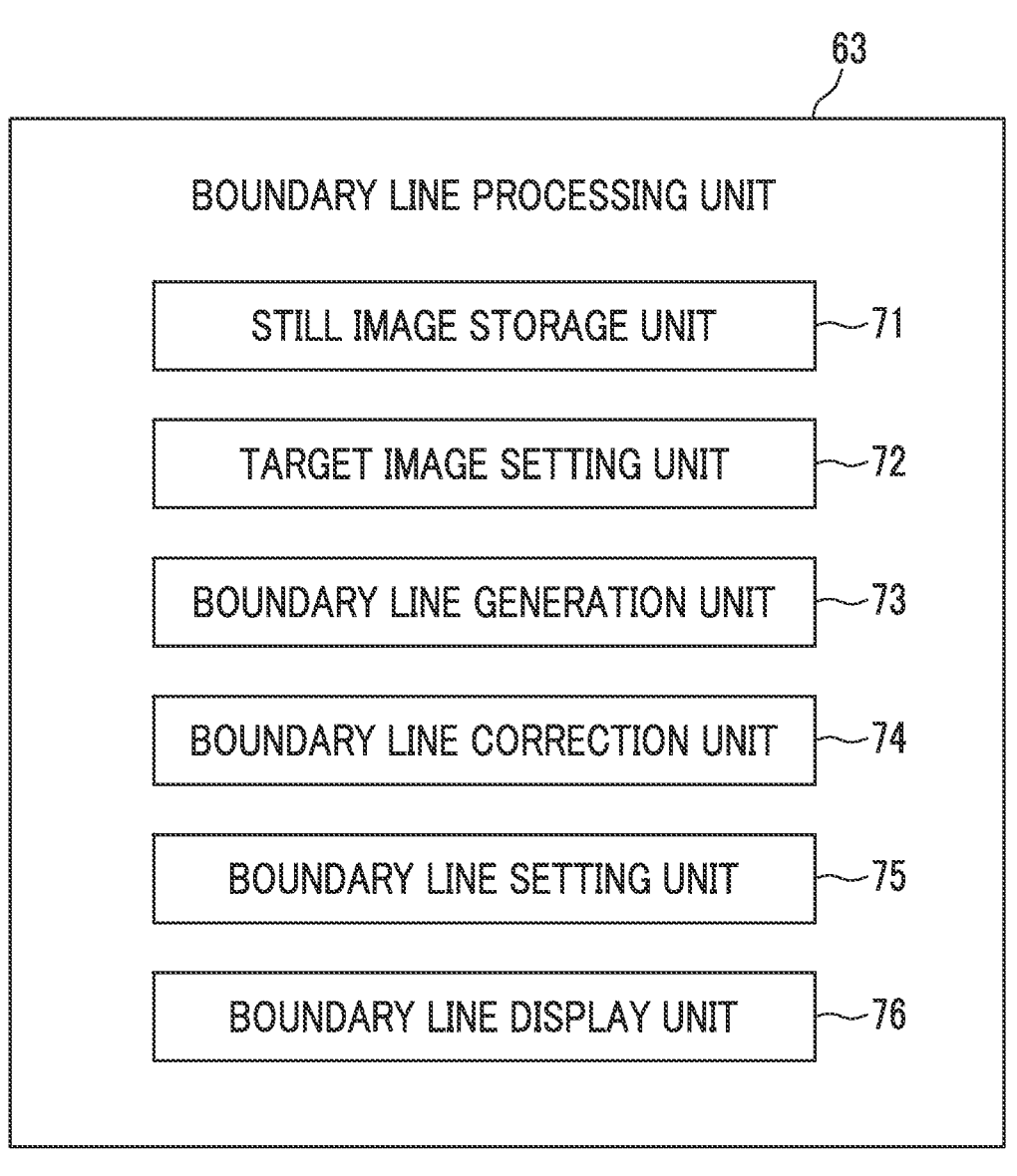
FIG. 6 is a block diagram showing a function of a boundary line processing unit.

As shown in FIG. 6, the boundary line processing unit 63 comprises a still image storage unit 71, a target image setting unit 72, a boundary line generation unit 73, a boundary line correction unit 74, a boundary line setting unit 75, and a boundary line display unit 76. The still image storage unit 71 stores the still image 19 as a target for setting the boundary line. The target image setting unit 72 sets a selected still image that is the still image 19 as the target for setting the boundary line. The boundary line generation unit 73 generates the boundary line of the selected still image. The boundary line correction unit 74 corrects the generated boundary line as needed. The boundary line setting unit 75 sets the generated or corrected boundary line and creates the boundary line display image. The boundary line display unit 76 displays the boundary line display image on the display device such as the display 15.

A user performs an observation by operating the mode selector switch 12g (see FIG. 1) or the like of the endoscope operation part 12b to perform switching for adding the observation support mode. In the observation support mode, the boundary line display image in which a boundary line is set in the acquired still image 19 can be created and displayed at a predetermined position of the display device such as the display 15.

The still image 19 can be acquired in an examination being performed at that time or acquired in the past examination. The still image acquired in the examination being performed at that time is acquired in the same examination as the video image and is selected from the still images 19 acquired in the examination by the user. The still image 19 acquired in the past examination can be used by calling up the still image 19 stored in the still image storage unit 71. The still image 19 acquired in the past examination can be, for example, the still image 19 having the region of interest such as a similar site or a similar lesion to the observation target in the current examination, the past still image 19 of the same site as the site of a patient being examined, or the like.

The selected still image may be obtained by displaying one or a plurality of still images 19 on the display 15 and selecting a selected still image from the displayed still images 19, or by displaying one or a plurality of still images 19 on a touch panel 91 of the tablet 17 and selecting a selected still image from the displayed still images 19. The still image 19 or the like displayed on the touch panel 91 of the tablet 17 can also be displayed on the display 15 via the processor device 14, and the images displayed on the two can be synchronized.

Figure 7:
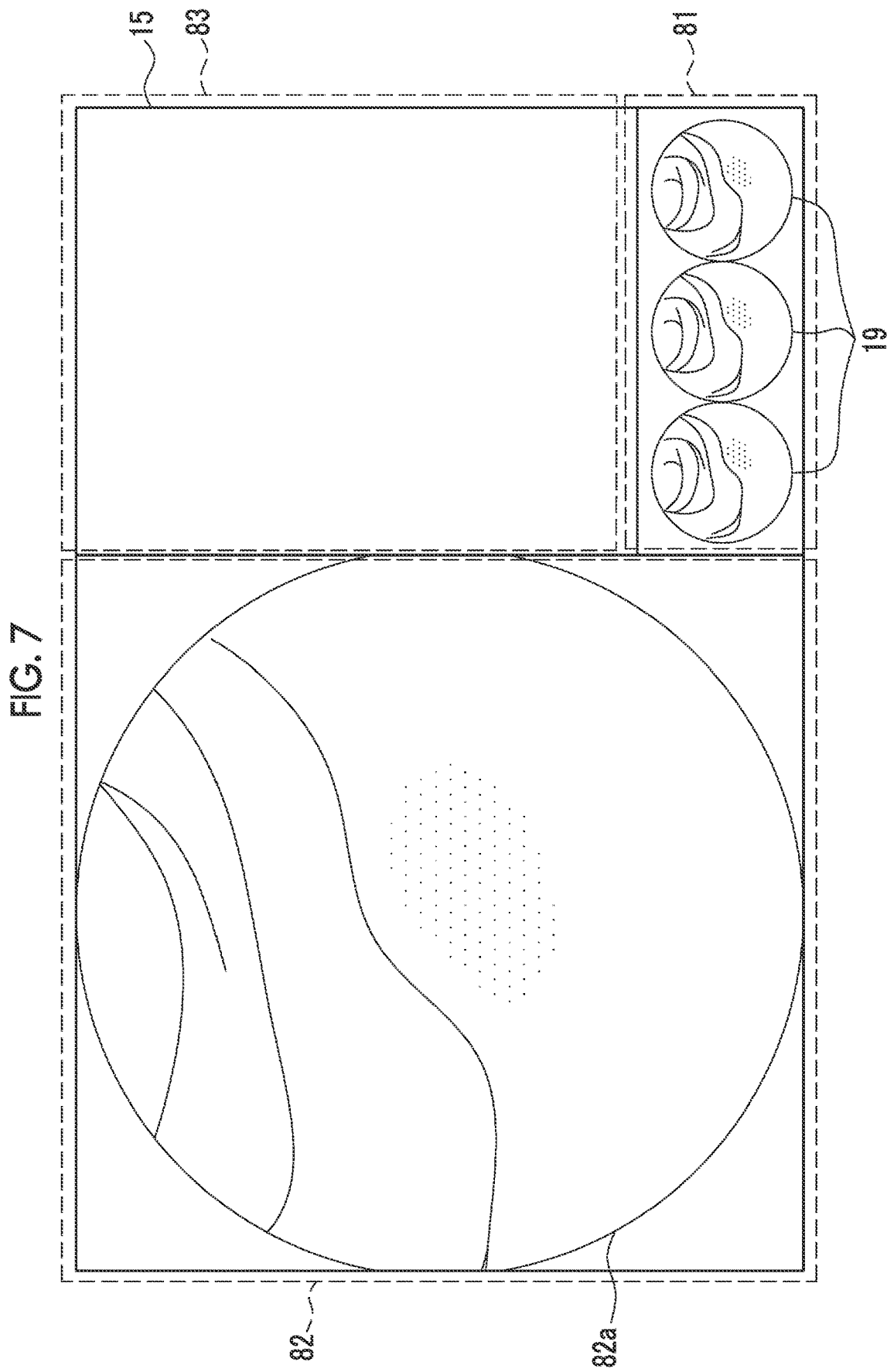
FIG. 7 is an image diagram of a display including a still image.

In the present embodiment, the still image 19 is acquired in a case where the user operates the freeze switch 12i (see FIG. 1). The acquired still image 19 is stored in the still image storage unit 71. As shown in FIG. 7, the still images 19 stored in the still image storage unit 71, for example, three still images 19 acquired most recently, are displayed in a temporary display still image region 81 of the display 15 in an order of imaging time. In a case where the still image 19 is newly acquired, the still image 19 with the oldest imaging time among the three still images 19 displayed in the temporary display still image region 81 is deleted, and instead, the newly acquired still image 19 is displayed. The display 15 comprises a live video region 82 where a video image 82a of the endoscopic image is displayed and a fixed display still image region 83 where the selected still image or the boundary line display image is displayed. The selected still image is an image for which the boundary line 18 is set.

Next, the target image setting unit 72 sets the still image 19 selected from the still images 19 stored in the still image storage unit 71, as the selected still image. Examples of a method of selecting and setting the selected still image from the three still images 19 displayed in the temporary display still image region 81 include a method of setting one still image 19 with a cursor or the like in the temporary display still image region 81 displayed on the display 15 or a method of setting one still image 19 using the tablet 17. A preferred method can be selected depending on various situations, such as whether a person other than an operator of the endoscope can perform the operation.

Figure 8:
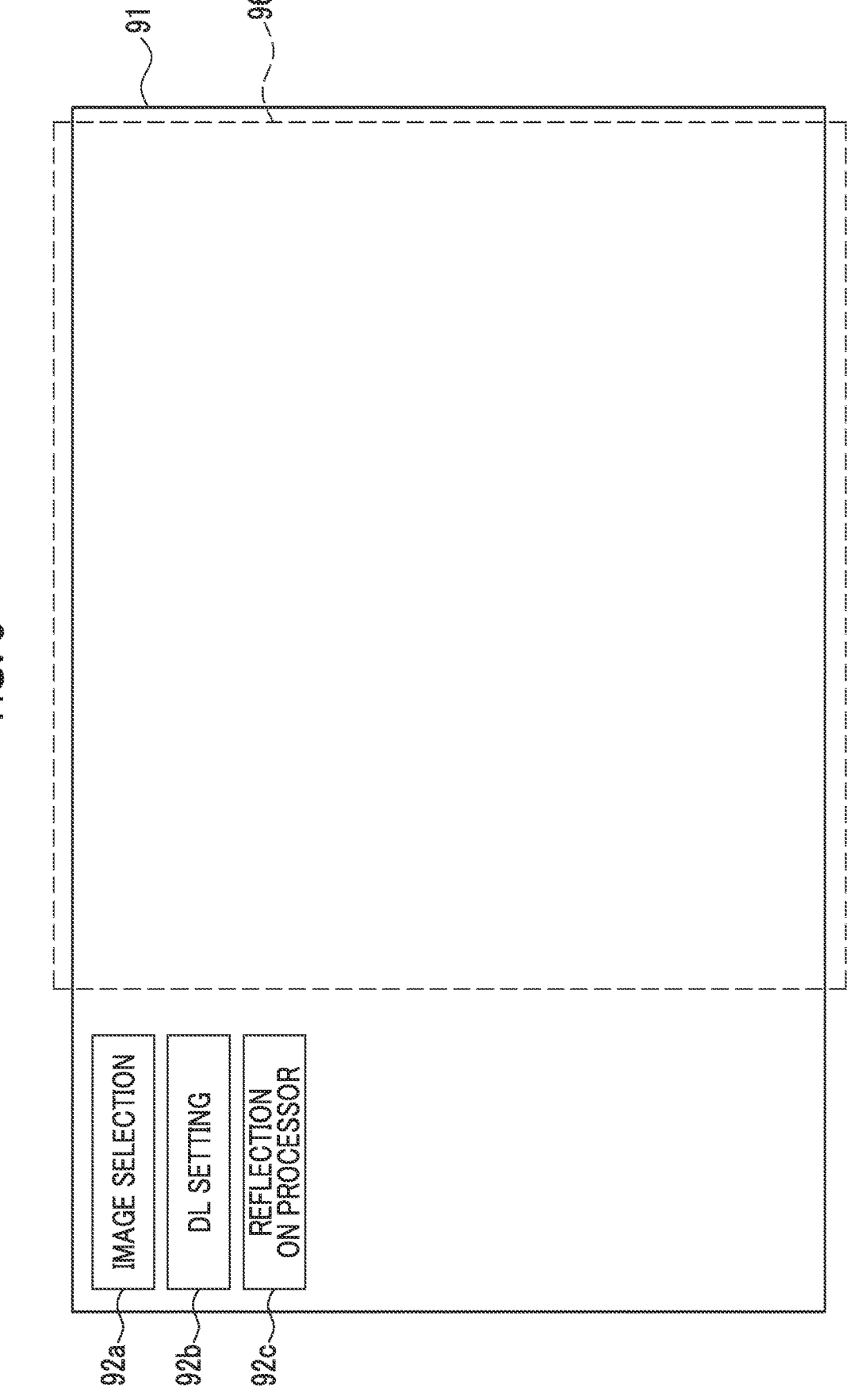
FIG. 8 is an image diagram of a touch panel including a home screen.

In the present embodiment, the selected still image is set by using the tablet 17. As shown in FIG. 8, a home screen displayed on the touch panel 91 of the tablet 17 comprises an image selection button 92a, a demarcation line (DL)

setting button 92b, and a reflection-on-processor button 92c. Further, a selected still image region 96 where the selected still image is displayed is provided. The image selection button 92a is a button for selecting the selected still image. The DL setting button 92b is a button for setting the boundary line 18. The reflection button on processor 92c is a button for sending the set boundary line 18 to the processor device 14 and displaying the boundary line 18 on the display 15.

Figure 9:
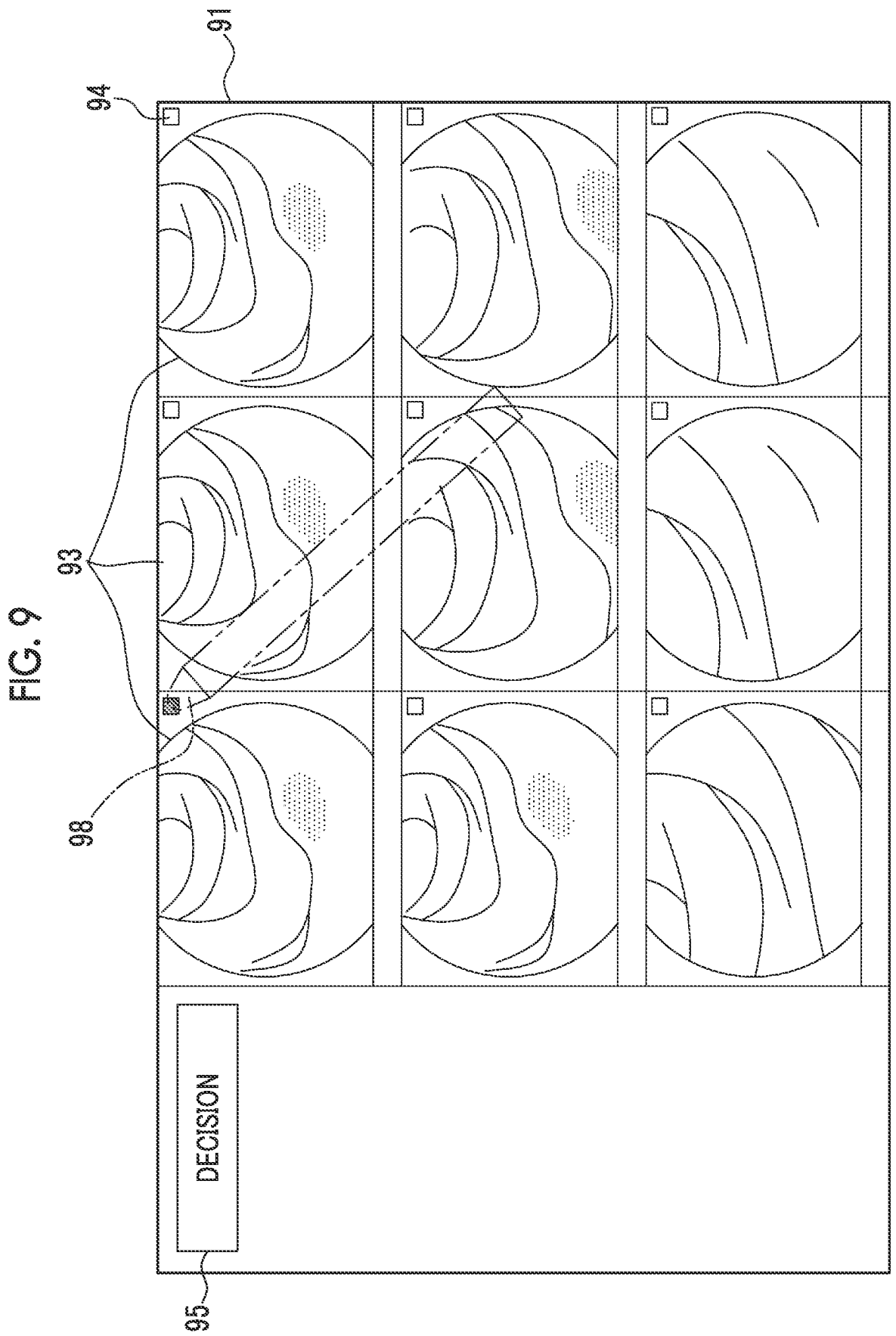
FIG. 9 is an image diagram of the touch panel including a thumbnail.

By pressing the image selection button 92a on the home screen of the touch panel 91 of the tablet 17, as shown in FIG. 9, the still images 19 stored in the still image storage unit 71, for example, a predetermined number of thumbnails 93, are displayed on the screen of the touch panel 91 in the order of imaging time. Note that in the diagram, in order to avoid complication, the reference numerals may be attached only to some parts. In a case where one check box 94 among the thumbnails 93 of the still images 19 is touched with a touch pen 98 or the like, one of the thumbnails is selected. After that, by pressing a decision button 95, the still image 19 of the selected thumbnail 93 can be selected as the selected still image.

Figure 10:
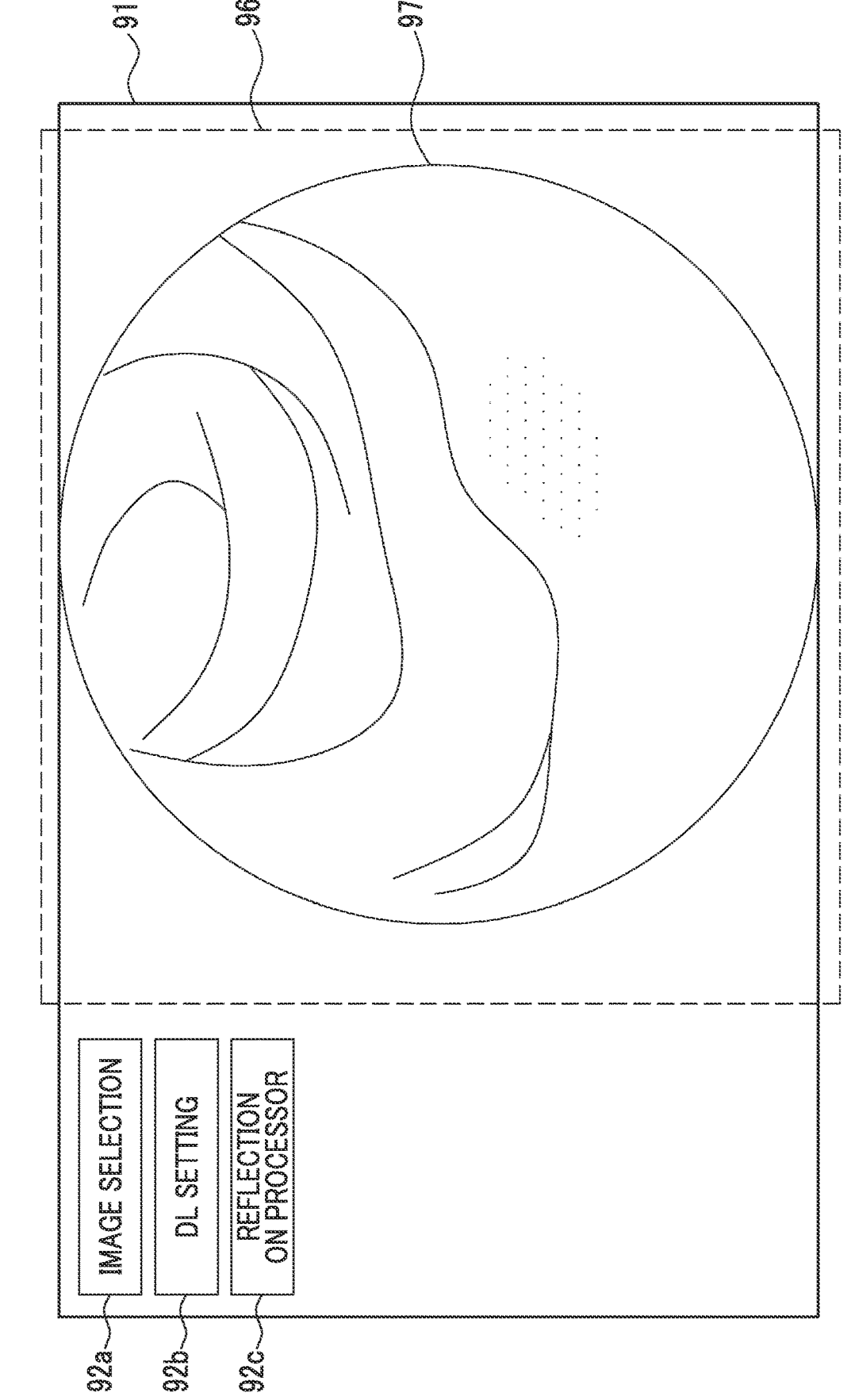
FIG. 10 is an image diagram of the touch panel including a selected still image.

As shown in FIG. 10, after the decision button 95 is pressed, the screen of the tablet 17 returns to the home screen, and the selected still image 19 is displayed as a selected still image 97 in the selected still image region 96.

Figure 11:
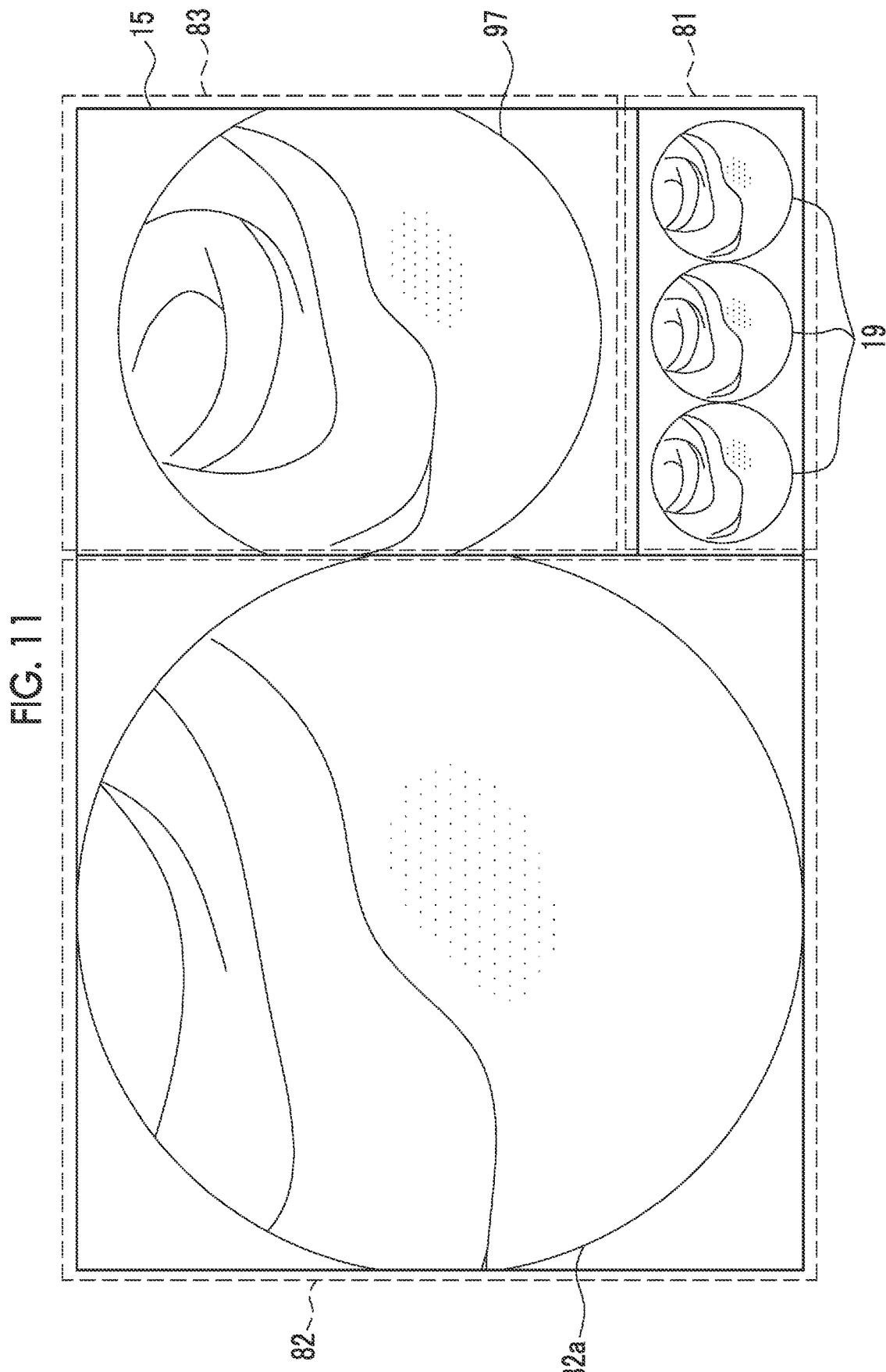
FIG. 11 is an image diagram of the display including the selected still image.

Next, in a case where a reflection-on-processor button 92c provided on the home screen of the tablet 17 is pressed, information on the selected still image 97 is sent to the processor device 14. As shown in FIG. 11, the processor device 14 continuously displays the selected still image 97 in the fixed display still image region 83 of the display 15. Therefore, on the display 15, the current video image 82a of the endoscope is displayed in the live video region 82, the selected still image 97 is continuously displayed in the fixed display still image region 83, and three still images 19 acquired most recently are displayed in the temporary display still image region 81 while being updated.

Next, the boundary line generation unit 73 generates the boundary line 18 based on the selected still image 97, that is, the still image 19 displayed in the fixed display still image region 83 of the display 15. Examples of a method of generating the boundary line 18 include an automatic method of detecting and generating the boundary line 18 based on the selected still image 97 or a manual method of generating the boundary line 18 through user drawing on the selected still image 97.

Figure 12:
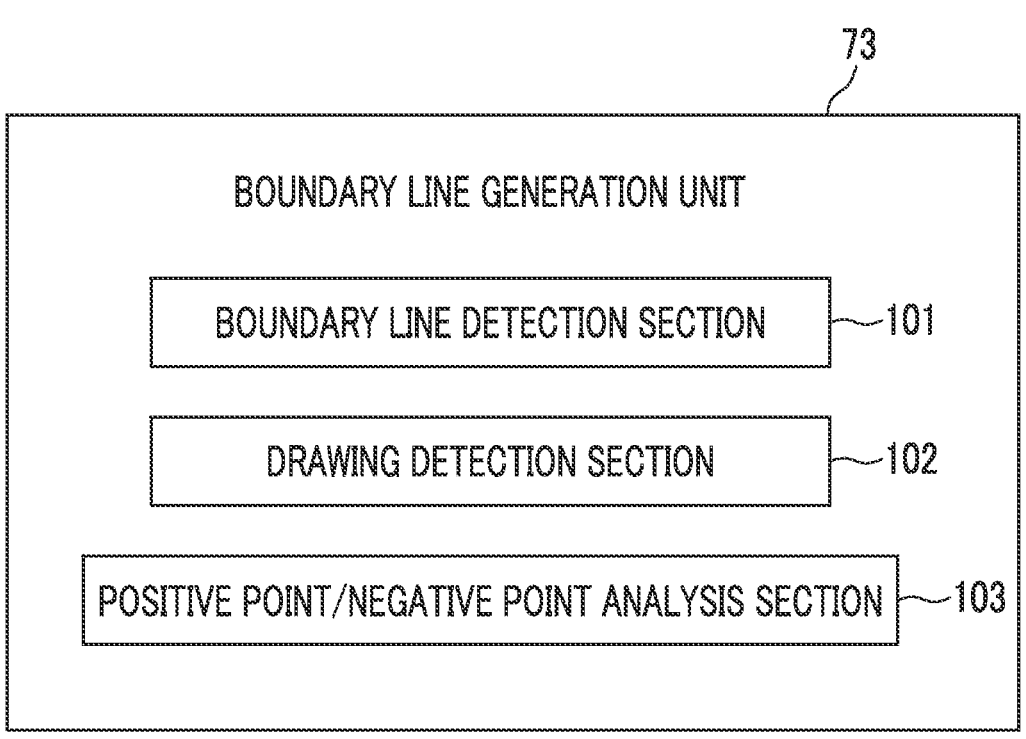
FIG. 12 is a block diagram showing a function of a boundary line generation unit.

As shown in FIG. 12, the boundary line generation unit 73 comprises a boundary line detection section 101, a drawing detection section 102, and a positive point/negative point analysis section 103. The boundary line detection section 101 detects the boundary line 18 of the selected still image 97 based on the selected still image 97 and sets the boundary line 18. The drawing detection section 102 detects the boundary line 18 obtained through drawing and sets the boundary line 18. The positive point/negative point analysis section 103 detects the boundary line 18 by analyzing the drawing of a positive point, which is generated in the region of interest of the selected still image 97 through the user's determination, and/or the drawing of a negative point, which is generated in the region of disinterest of the selected still image 97 through the user's determination, and sets the detected boundary line 18.

The boundary line detection section 101 automatically detects the boundary line through calculation based on the selected still image 97 in a case where information on the boundary line is not associated with the selected still image 97. In a case where information on the boundary line, such as the still image 19 in the past examination, is associated, the boundary line detection section 101 reads the information on the boundary line. In the present embodiment, since the selected still image 97 is based on the still image 19 acquired during the examination, the boundary line is detected from the selected still image 97. As a method of detecting the boundary line, a method using image processing, a method using a learning model based on machine learning, or the like can be used, and any method may be employed as long as the boundary line in the selected still image can be detected.

As the method using image processing, for example, diagnostic techniques based on endoscopic findings can be used. In a case of VS classification for diagnosing gastric cancer, the diagnosis is performed by combining references (Regular, Irregular, and Absent) for microvascular architecture (V: microvascular (MV) architecture) and references (Regular, Irregular, and Absent) for a microsurface structure (S: microsurface (MS) structure) in endoscopic findings. For example, in a case where both V and S are classified as "Regular", a diagnosis is made that it is a hyperplastic polyp rather than cancer.

Therefore, in the method using image processing, the glandular structures and/or vascular structures of the observation target are extracted based on the selected still image 97, and non-continuous points are calculated by using the density distribution and/or shape distribution of these structures. The non-continuous point can be calculated by edge detection or the like. The calculated non-continuous points are connected to generate a closed curve. Since the boundary line 18 is a boundary between a lesion and a non-lesion, this closed curve can be used as the boundary line 18.

Figure 13:
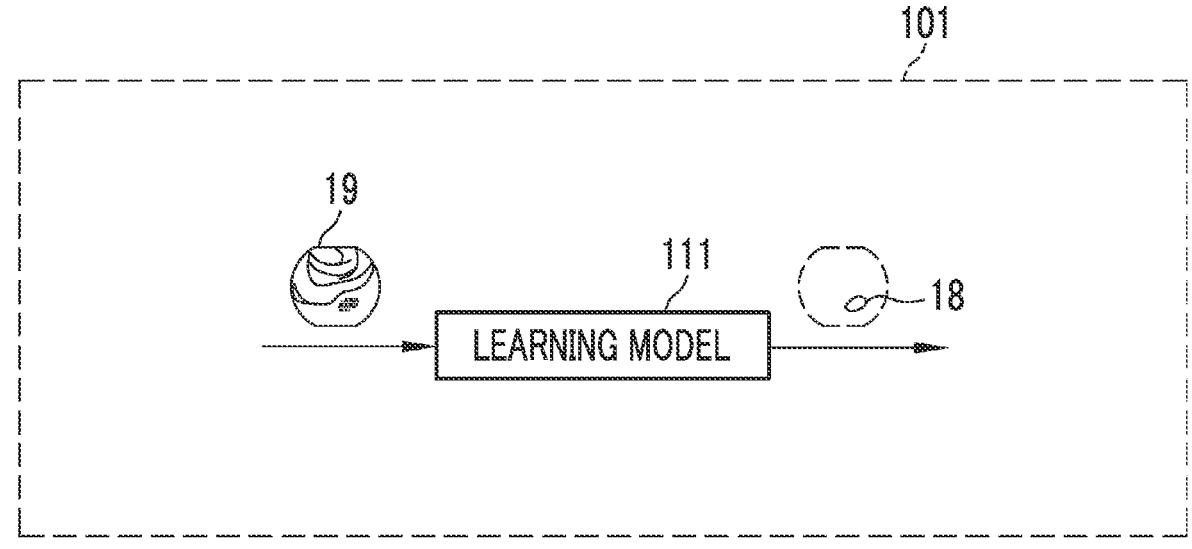
FIG. 13 is an explanatory diagram illustrating a function of a learning model.

As the method using machine learning, as shown in FIG. 13, a learning model 111 that outputs the boundary line 18 in a case where the still image 19 is input can be created and used. Since the selected still image 97 is the still image 19, the learning model 111 outputs the boundary line 18 in the selected still image 97 in a case where the selected still image 97 is input.

The learning model 111 can be based on supervised learning, unsupervised learning, or the like. The learning model 111 based on supervised learning is generated by learning a learning still image in which information regarding the boundary line 18 is associated with the still image 19. The information regarding the boundary line 18 also includes information associated with the fact that the still image 19 does not include the boundary line 18. After the learning, a test is performed using a still image 19 for which the boundary line 18 is already known, and various adjustments such as parameters are performed. After the adjustment, the learning model 111 is generated by further performing various adjustments such as parameters such that the boundary line 18 is correctly output in a case where the still image 19 for which the boundary line 18 is unknown is input. In the learning model 111 based on unsupervised learning, a machine learning technique such as clustering can be used.

It should be noted that the learning model 111 is preferably a neural network model. In addition, a convolutional neural network is preferable because the learning model 111 detects the boundary line 18 based on the still image 19. Therefore, the learning model 111 preferably has a layered structure having an output layer that outputs the boundary line 18 and at least one intermediate layer. Further, a deep learning model is preferable because there is a probability of a more excellent detection result.

The drawing detection section 102 generates the boundary line 18 through user drawing on the selected still image 97. It is preferable that the drawing is performed with the tablet 17 having the touch panel 91. In a case where the selected still image 97 is decided on, the selected still image 97 is displayed in the selected still image region 96 on the home screen shown on the touch panel 91 of the tablet 17 (see FIG. 10).

Examples of the drawing method include a method through user drawing on the selected still image 97 displayed on the tablet 17. The drawing can be a line drawing, a point drawing, a figure, or the like. For example, the user can make a determination through visual observation of the still image 19 and draw the line drawing on the region of interest, thereby obtaining this line drawing as the boundary line 18.

In addition, it is possible to employ a method of generating the boundary line 18 by analyzing the positive point and/or the negative point drawn by the user on the selected still image 97 displayed on the tablet 17 through the positive point/negative point analysis section 103. The positive point is a point determined by the user through the visual observation of the still image 19 and drawn in the region of interest. The negative point is a point determined by the user through the visual observation of the still image 19 and drawn in the region of disinterest.

Figure 14:
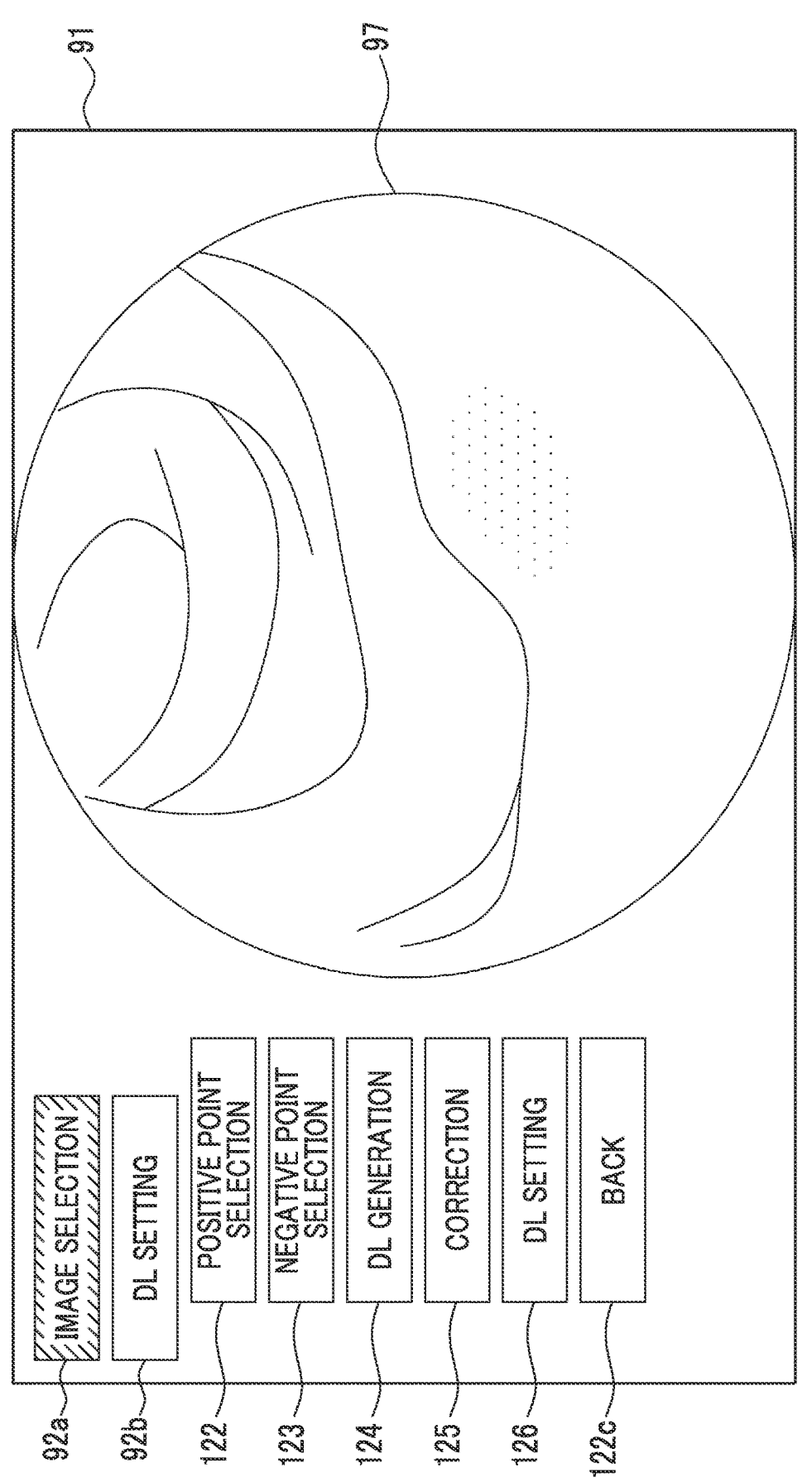
FIG. 14 is an image diagram of the touch panel including a DL setting button.

As shown in FIG. 14, the touch panel 91 of the tablet 17 is provided with the DL setting button 92*b* for setting the boundary line 18. In a case where the DL setting button 92*b* is pressed, a positive point selection button 122, a negative point selection button 123, a DL generation button 124, a correction button 125, a DL setting button 126, and a back button 122*c* are displayed. The positive point selection button 122 is a button for registering the positive point on the selected still image 97, and the negative point selection button 123 is a button for registering the negative point on the selected still image 97. The DL generation button 124 is a button for generating the boundary line 18 based on the registered positive point and/or negative point. The correction button 125 is a button for correcting the generated boundary line 18. The DL setting button 126 is a button for sending the generated boundary line 18 to the processor device 14 and synchronously updating the selected still image 97 displayed on the display 15. The back button 122*c* is a button for returning to the home screen of the tablet 17. A configuration may be employed to prevent an erroneous operation, such as disabling the image selection button 92*a* from being pressed upon pressing the DL setting button 92*b*.

Figure 15:
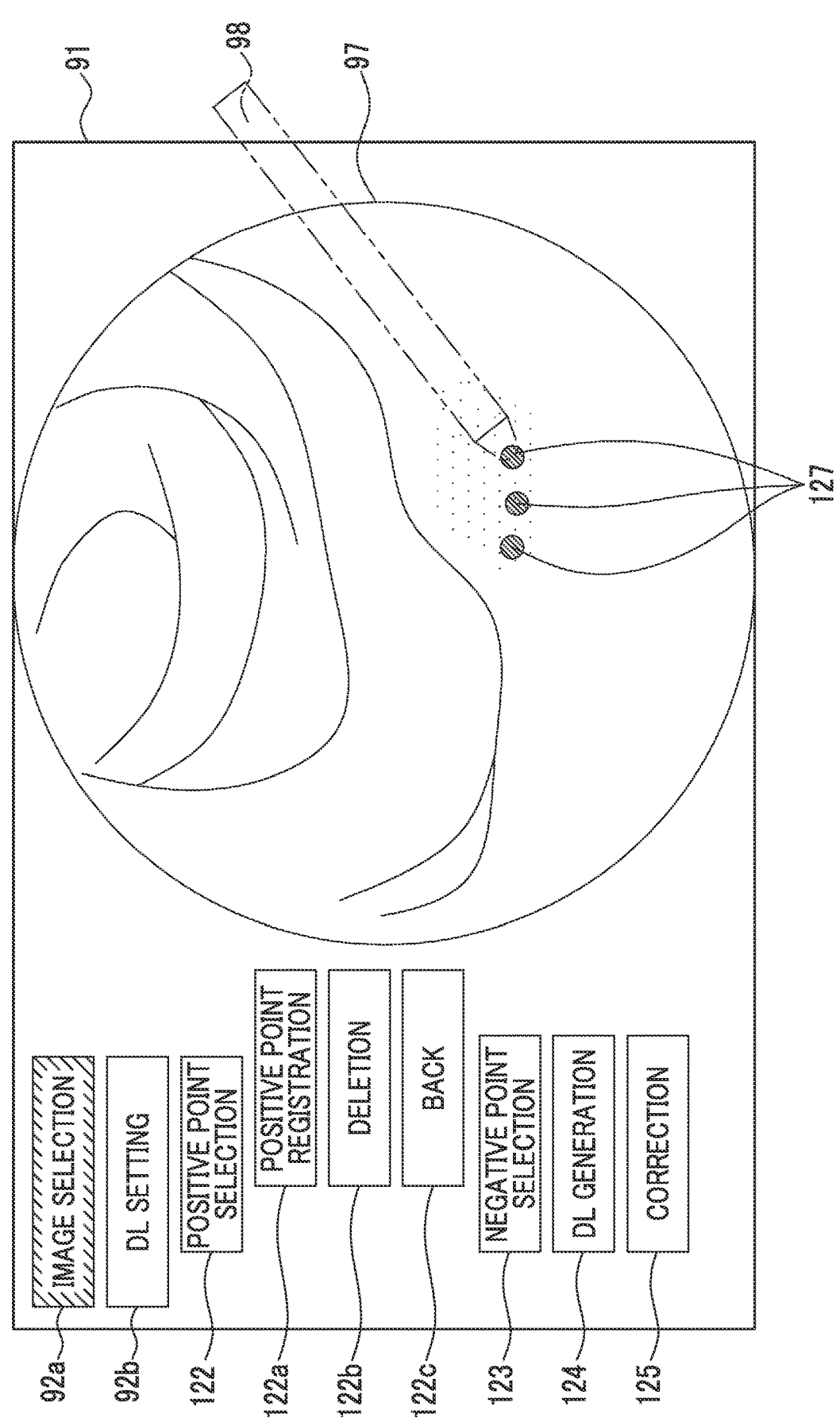
FIG. 15 is an image diagram of the touch panel including a positive point registration button.

As shown in FIG. 15, in a case where the selected still image 97 is displayed on the touch panel 91, a positive point registration button 122*a*, a deletion button 122*b*, and the back button 122*c* are displayed upon pressing the positive point selection button 122. The positive point registration button 122*a* is a button for registering the positive point drawn on the selected still image 97. The deletion button 122*b* is a button for deleting the registered positive point. The back button 122*c* is a button for returning to the previous screen by one stage.

In a case where the positive point selection button 122 is pressed, the positive point 127 can be drawn at a touched location by touching the selected still image 97 with a finger, the touch pen 98, or the like. After the drawing, by pressing the positive point registration button 122*a*, this drawing is registered as a positive point 127. Here, in a case where the back button 122*c* is pressed, the screen returns to a screen for selecting either the positive point 127 or the negative point (see FIG. 14).

Figure 16:
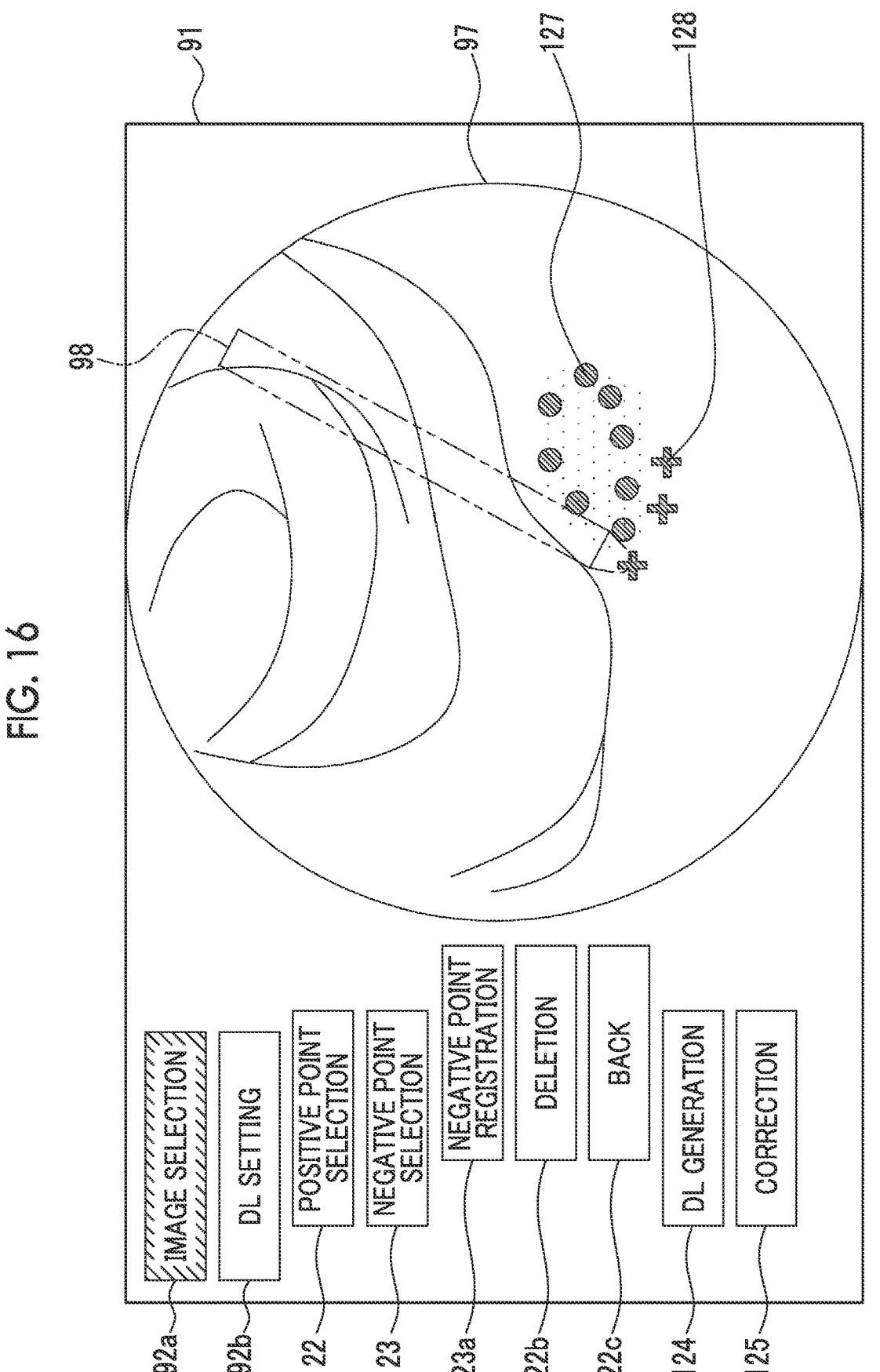
FIG. 16 is an image diagram of the touch panel including a negative point registration button.

As shown in FIG. 16, the negative point is also drawn by the same operation. In a case where the negative point selection button 123 is pressed, a negative point registration button 123*a* is displayed. By touching the selected still image 97, it is possible to draw a negative point 128 at a touched location. After the drawing, by pressing the negative point registration button 123*a*, this drawing is registered as the negative point 128.

As the positive point 127 and the negative point 128, only the positive point 127, only the negative point 128, or the positive point 127 and the negative point 128 can be drawn. One or a plurality of the positive points 127 and of negative points 128 can be drawn. The positive point/negative point analysis section 103 generates the boundary line 18 by analyzing the positive point 127 and/or the negative point 128. For example, the boundary line 18 is generated between the positive point 127 and the negative point 128. Therefore, it is preferable to draw a plurality of positive points 127 and of negative points 128. This is because there is a high probability that the positive point/negative point analysis section 103 generates a more accurate boundary line 18.

In addition, a technique such as image processing or machine learning may be combined with information on the positive point 127 and/or the negative point 128. Therefore, even in a case where one positive point 127 or one negative point 128 is drawn, by combining analysis using image processing based on the selected still image 97 or the learning model 111, a highly accurate boundary line 18 can be obtained.

The high accuracy of the boundary line 18 means that, for example, in a case where the region of interest is a lesion, the boundary between a lesion and a non-lesion in the observation target is more correctly shown in response to a temporal change, or is more correctly shown in terms of precision.

The selected still image 97 displayed on the touch panel 91 can be moved or enlarged by an operation on the screen, such as dragging or pinching, such that the user can easily determine the positive point 127 and/or the negative point 128 in the selected still image 97. The user can generate a more accurate boundary line 18 by determining the selected still image 97 in detail through enlargement or the like and by drawing a plurality of positive points 127 and/or of negative points 128 or drawing the positive point 127 and/or the negative point 128 in a more detailed manner.

In addition, during the endoscopic examination, a biopsy may be performed in a part of the region of interest, and the positive point 127 and/or the negative point 128 may be input based on the location of the biopsy and the result thereof. In this case, since more accurate information can be input for the positive point 127 and/or the negative point 128, a more accurate boundary line 18 can be set.

Figure 17:
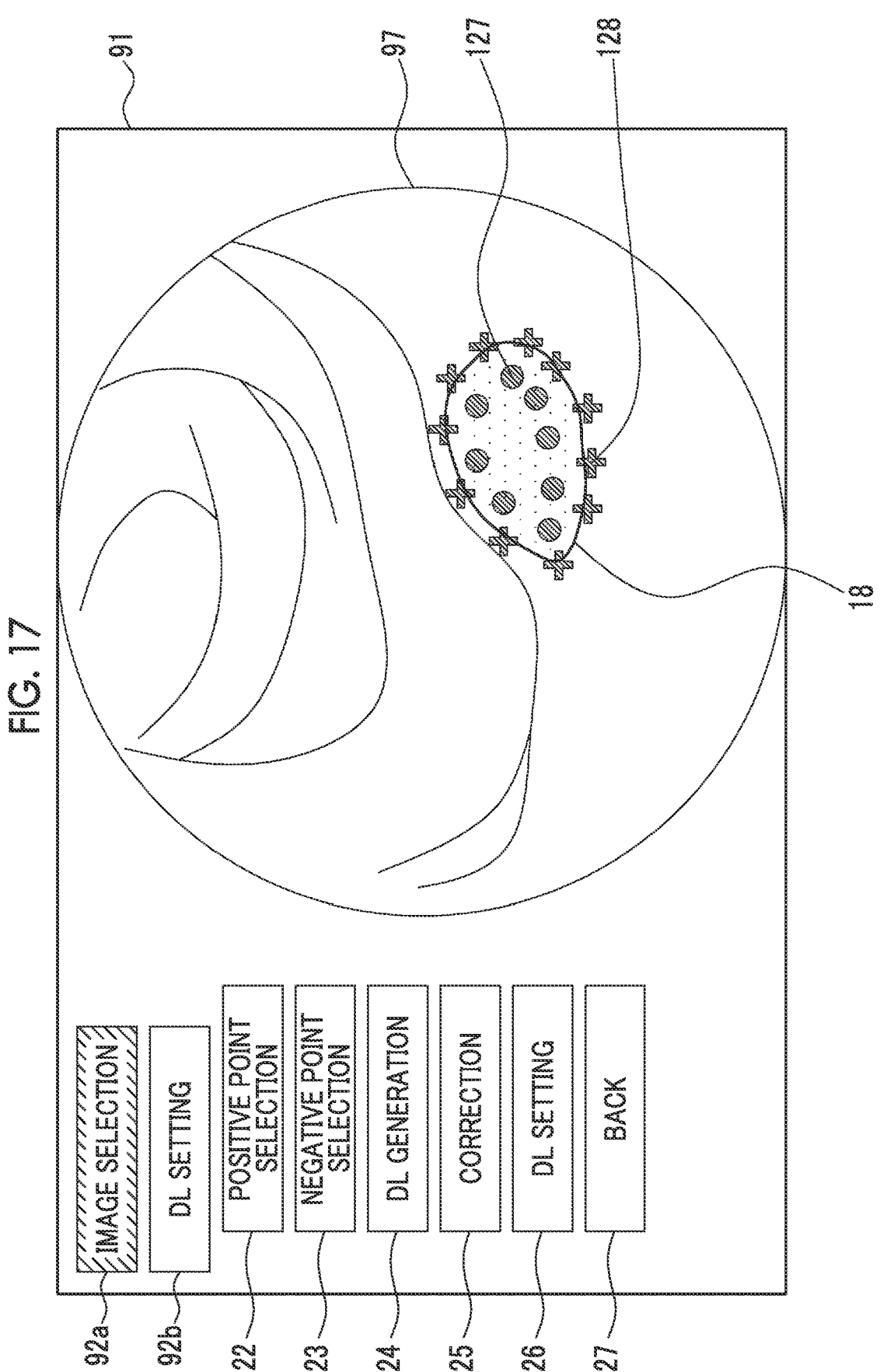
FIG. 17 is an image diagram of the touch panel including a generated boundary line.

As shown in FIG. 17, in a case where the drawing of the positive point 127 and/or the negative point 128 ends, the user presses a demarcation line (DL) generation button 124. As a result, the boundary line 18 generated by the positive point/negative point analysis section 103 is displayed on the selected still image 97.

Next, the boundary line setting unit 75 sets the generated boundary line 18. In the present embodiment, the user presses the DL setting button 126 in a case where the user considers that the generated boundary line 18 is appropriate. As a result, the boundary line 18 is set on the selected still image 97. In a case where the boundary line 18 is set, the display of the positive point 127 and the negative point 128 disappears. In a case where the work of setting the boundary line 18 is completed, the user presses the back button 122*c* to return to the home screen of the tablet 17.

Figure 18:
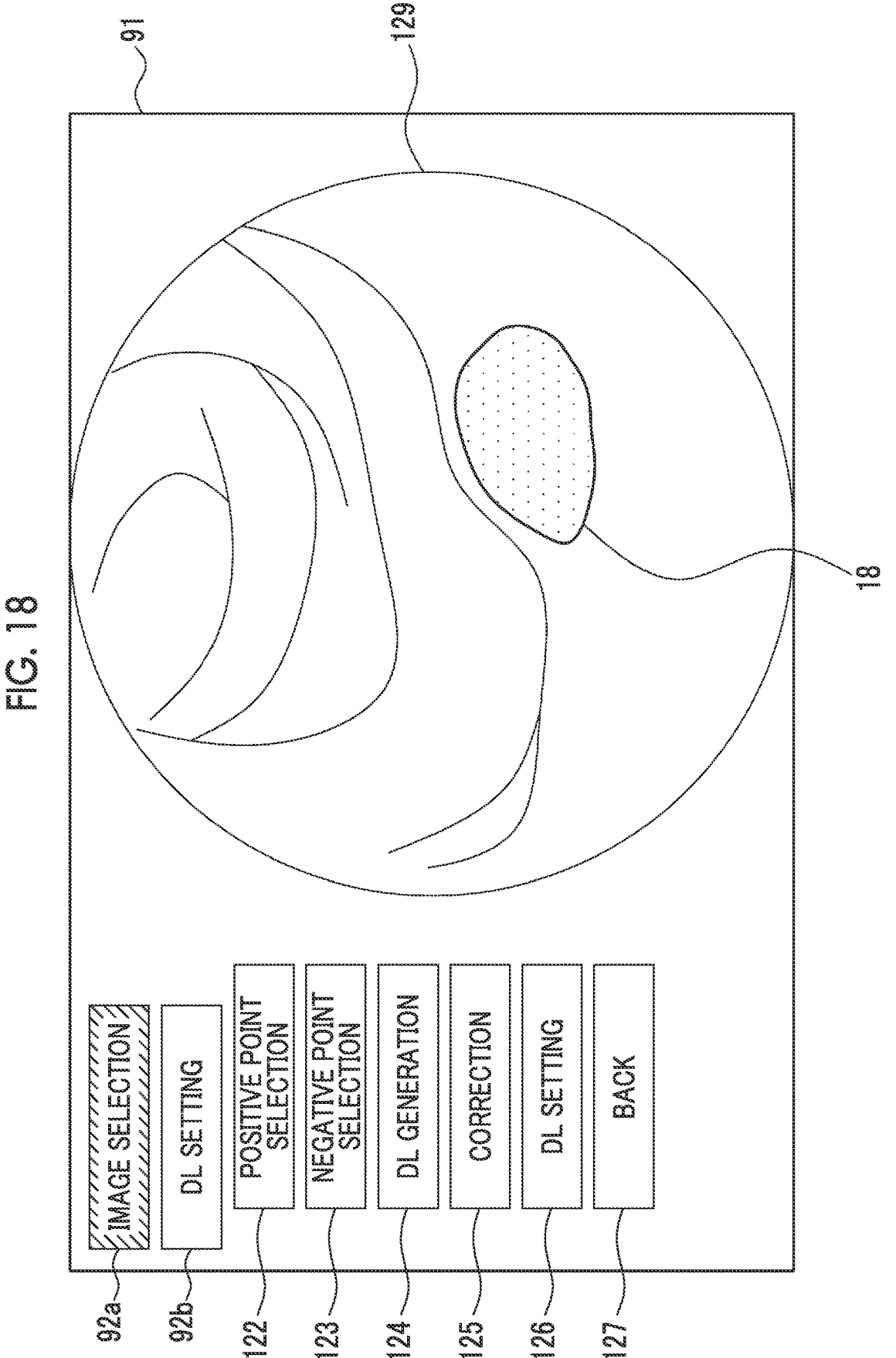
FIG. 18 is an image diagram of the touch panel including a boundary line display image.

As shown in FIG. 18, a boundary line display image 129 in which the boundary line 18 set in the selected still image 97 is displayed is displayed in the selected still image region 96 of the home screen. The boundary line display image 129 is an image in which the boundary line 18 is displayed on the still image 19.

Next, the boundary line correction unit 74 corrects the set boundary line 18 and sets the corrected boundary line 18 again. In a case where the user considers that the generated boundary line 18 is not appropriate, the user can correct the boundary line 18 to generate an appropriate boundary line 18.

Examples of the correction include a method of manually correcting the generated boundary line 18, a correction method based on the still image 19, or a correction method based on the boundary line display image 129 acquired in the past. Examples of the manual correction method include a method of manually moving and correcting the generated boundary line 18, or a method of correcting the boundary line 18 by enlarging, reducing, or rotating the boundary line 18. Examples of the correction method based on the still image 19 include a method of determining, for example, an anomaly degree indicating a difference, a feature amount, or the like related to a color, a shape, or a surface layer mucosal structure of the observation target in the selected still image 97, which is the still image 19 as a target for which the boundary line 18 is generated, and designating the anomaly degree by the user in a case of adjusting the boundary line 18 based on the anomaly degree.

Figure 19:
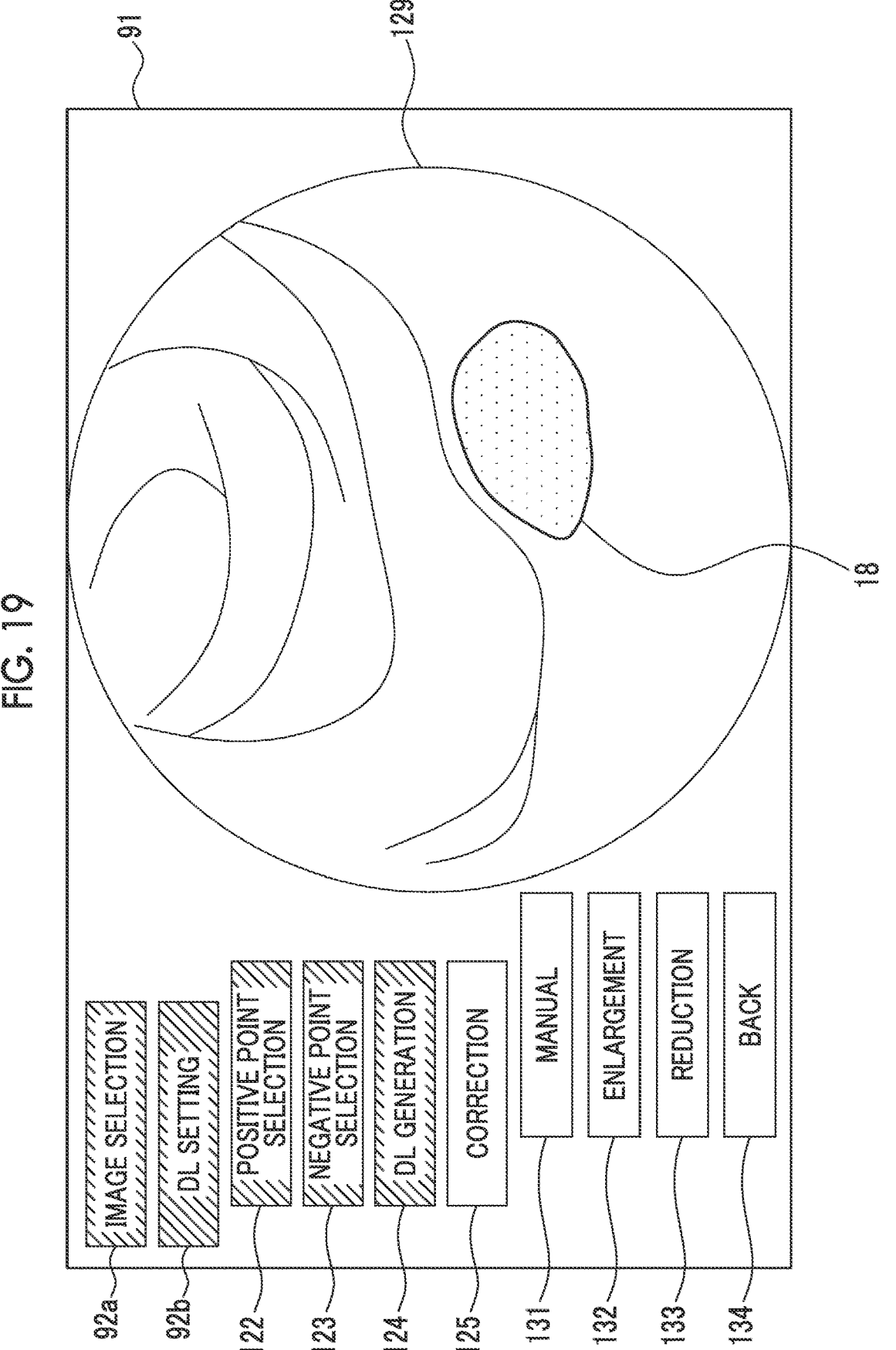
FIG. 19 is an image diagram of the touch panel including a correction button.

In a case of correcting the generated boundary line 18, the correction button 125 is pressed. As shown in FIG. 19, in a case where the correction button 125 is pressed, a manual button 131, an enlargement button 132, a reduction button 133, and a back button 134 are displayed. In a case where the manual button 131 is pressed, the boundary line 18 can be manually corrected. In a case where the enlargement button 132 is pressed, the boundary line 18 can be enlarged. Similarly, in a case where the reduction button is pressed, the boundary line 18 can be reduced.

Figure 20:
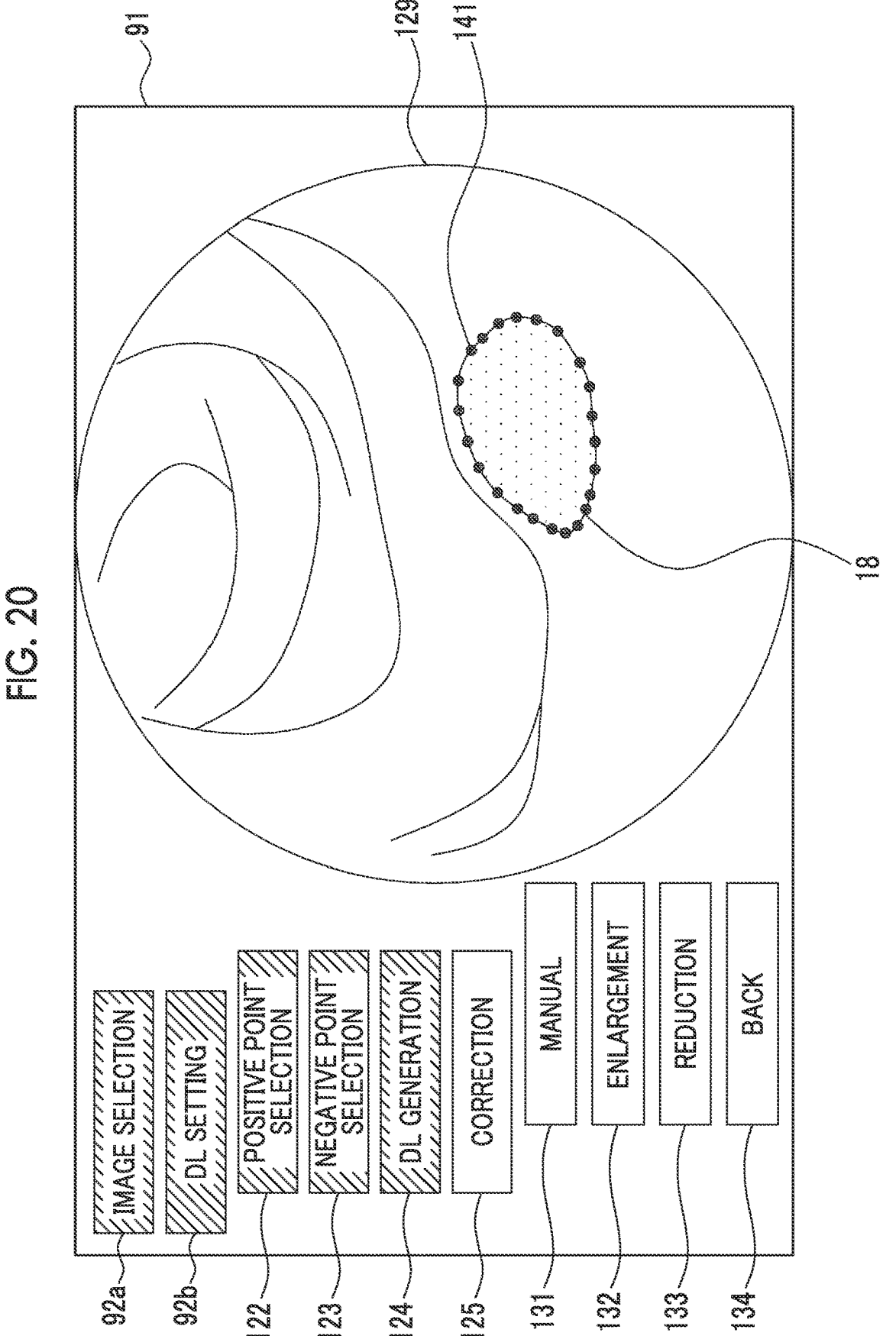
FIG. 20 is an image diagram of the touch panel including a boundary line with a vertex.
Figure 21:
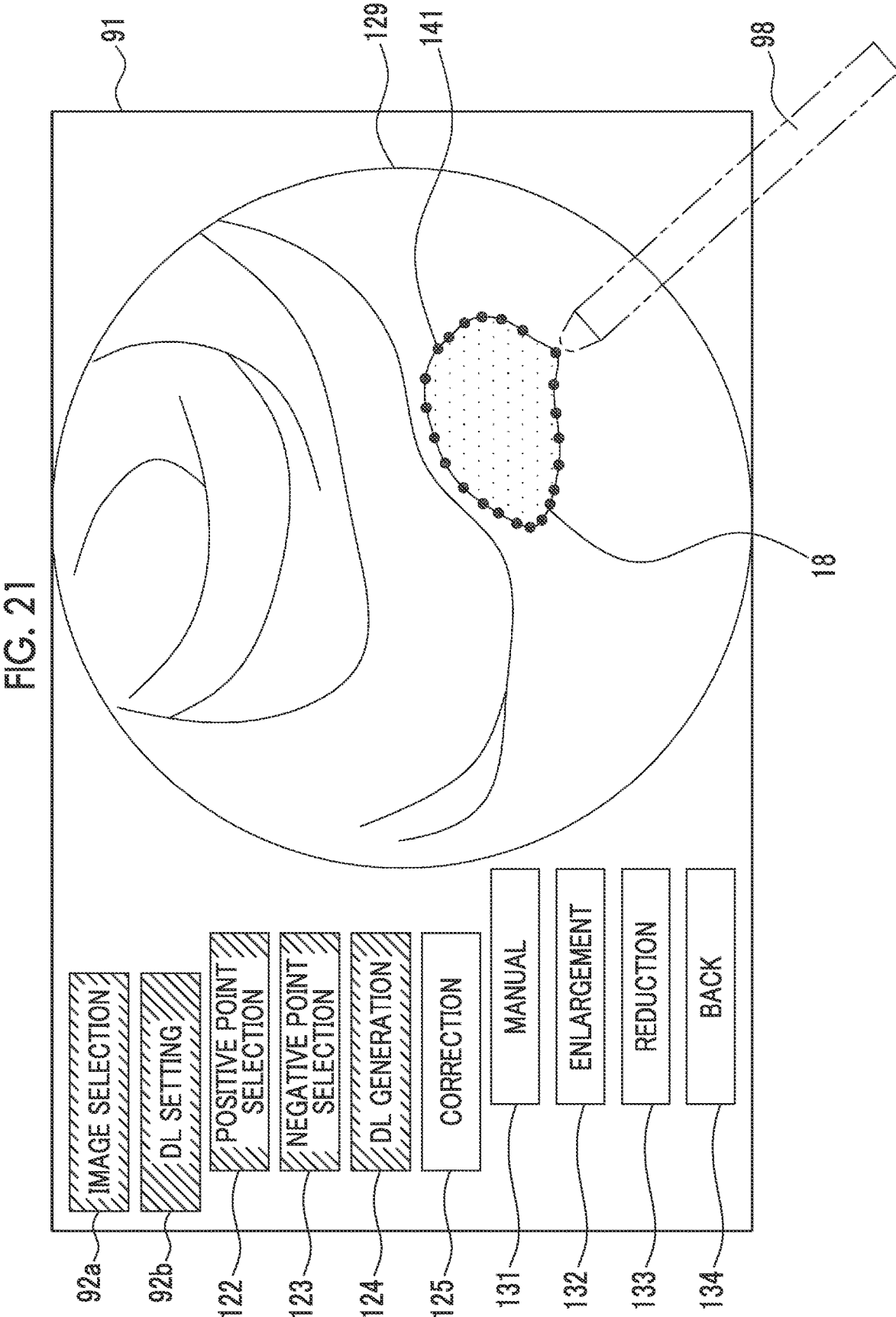
FIG. 21 is an image diagram of the touch panel including the moved vertex and the boundary line.

As shown in FIG. 20, in a case where the manual button 131 is pressed, a vertex 141 is displayed on the boundary line 18. As shown in FIG. 21, by dragging the vertex 141 with a finger, the touch pen 98, or the like, the boundary line 18 can be moved. In a case where the correction of the boundary line 18 is completed, by pressing the back button 134, the screen returns to the previous screen by one.

Figures 22, 23:
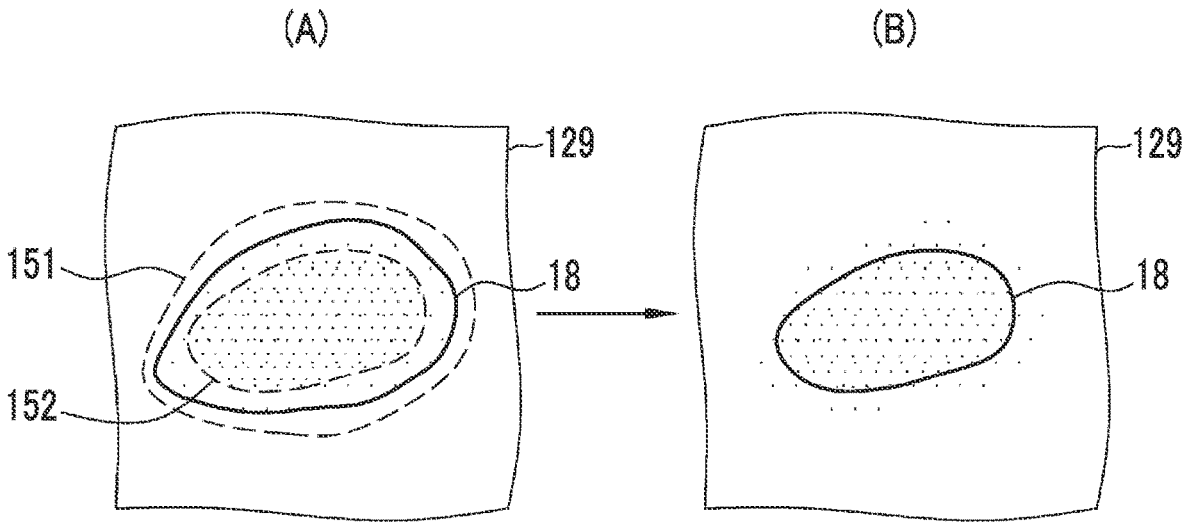
FIG. 22 is a block diagram showing a function of a boundary line correction unit.
FIG. 23 is an explanatory diagram illustrating display of an anomaly degree.

As the method of correcting the generated boundary line 18 based on the still image 19, it is possible to use the anomaly degree indicating a difference or other feature amounts related to a color, a shape, or a surface layer mucosal structure of the observation target. As shown in FIG. 22, the boundary line correction unit 74 comprises an anomaly degree determination section 142. The anomaly degree determination section 142 determines the anomaly degree based on the still image 19. In the present embodiment, the anomaly degree is determined based on the selected still image 97, which is the still image 19 for which the boundary line 18 is generated. The determined anomaly degree is represented by a numerical value. Therefore, in the selected still image 97, a region can be divided based on the anomaly degree through the determination of the anomaly degree determination section 142.

For example, in the region of interest, a region where the severity of a disease is high may have stronger erythema in the color of the mucous membrane than a region where the severity is low. Local injection for ESD may be performed into a lesion portion, which is the region of interest of the selected still image 97. The locally injected portion has a raised shape compared to its surroundings. In a case of the anomaly degree determination section 142 that determines the shape, a portion having a raised shape compared to its surroundings is determined to have a high anomaly degree. The larger the raised shape is, the higher the anomaly degree is given, and the smaller the raised shape is, the lower the anomaly degree is given. Therefore, in a case of correcting the generated boundary line 18, the user can decide which range to correct the boundary line 18 by designating the numerical value or the numerical value range of the anomaly degree. In a case of the present embodiment, the anomaly degree is divided into five stages, ranging from the anomaly degrees 1 to 5, based on the numerical range. As shown in (A) of FIG. 23, in the boundary line display image 129, the boundary line 18 is displayed in the region of interest, and a region 151 with the anomaly degree 1 and a region 152 with the anomaly degree 3 exist around the boundary line 18 and are displayed with temporary lines in response to the user's instruction. As shown in (B) of FIG. 23, in a case where the user designates the anomaly degree 3, the boundary line 18 is corrected into the region with the anomaly degree 3. By designating the anomaly degree, the user can accurately and easily perform corrections to the desired boundary line 18.

In addition, as the method using the anomaly degree, the following method can also be employed. For example, in a case where the boundary line display image 129 acquired in the past has the boundary line 18 generated without using the anomaly degree, such as an image obtained by manually drawing the boundary line 18 on the still image 19 by the user, first, the boundary line 18 is automatically generated on the boundary line display image 129 acquired in the past, and then the anomaly degree is determined. Then, it is examined which numerical value for the anomaly degree the automatically generated line of the boundary line 18 corresponds to. Then, the boundary line 18 is generated for the newly acquired still image 19 based on the anomaly degree examined as described above.

In addition, examples of the method of correcting the boundary line 18 based on the boundary line display image 129 acquired in the past include a method of reading the boundary line display image 129 acquired in the past and performing registration on the still image 19 acquired in the current examination to reflect the boundary line 18 onto the still image 19, or a method of reading the still image 19 associated with the positive point and/or the negative point acquired in the past and performing registration on the still image 19 acquired in the current examination to reflect the positive point and/or the negative point onto the still image 19.

With the above method, in a case where a preferred boundary line 18 has been generated in the past, a desired boundary line 18 can be accurately and easily corrected using information on the past boundary line 18 in the same observation target. The method of correcting the boundary line 18 as described above may be applied to a case where the boundary line 18 is generated.

With the configuration as described above, the correction of the boundary line 18 can be easily and quickly performed with a high degree of freedom. There are cases where, depending on the application of the boundary line 18, user preferences, or the like, it may be desired to display the boundary line 18 with a margin from the lesion or to display the boundary line 18 right at the edge of the lesion. The correction of the generated boundary line 18 can be freely and easily performed on the field, which is preferable because the boundary line 18 suitable for various needs can be generated.

In a case where the boundary line 18 is set based on the drawing, it is preferable that the drawing has been subjected to smoothing processing. The smoothing processing, also referred to as smoothing, is processing of smoothing the drawing and specifically, is processing of smoothly connecting stair-like portions in the drawing. By the smoothing processing, even the boundary line 18 obtained through hand drawing can be a smooth boundary line 18. Specific examples of the method include a method realized by entirely or partially averaging the coordinates of the boundary line 18 obtained through hand drawing or the feature amounts.

Even in a case where the generated boundary line 18 is corrected, the user presses the DL setting button 126 in a case where the user considers that the generated boundary line 18 is appropriate. In a case where the work of setting the boundary line 18 is completed, the user presses the back button 122c to return to the home screen of the tablet 17. On the home screen of the tablet, the boundary line display image 129 is displayed in the selected still image region 96 (see FIG. 19). In this case, the boundary line display image 129 is transmitted to the processor device 14 by pressing the reflection-on-processor button 92c.

Figure 24:
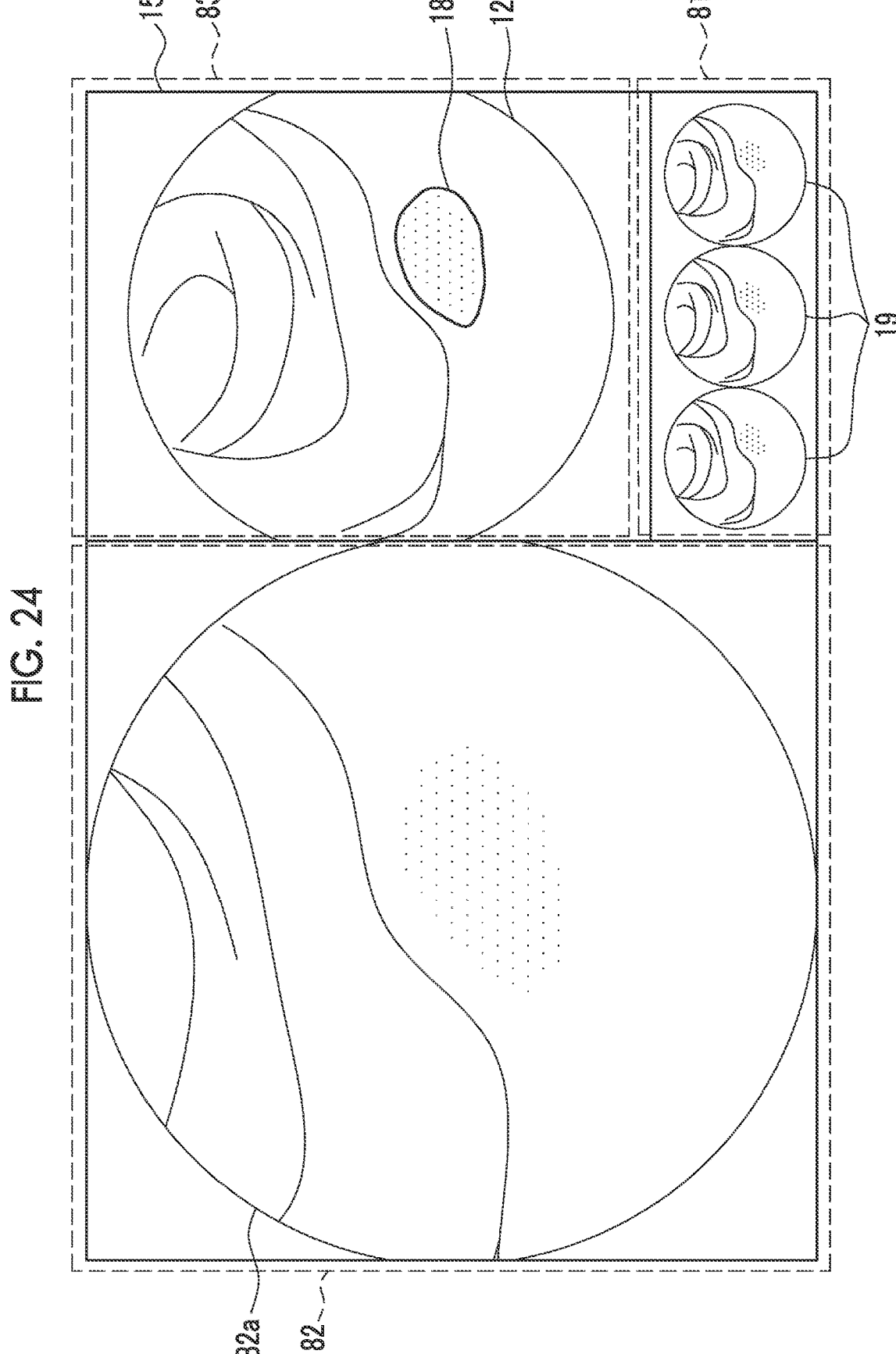
FIG. 24 is an image diagram of the display including the boundary line display image.

Next, the boundary line display unit 76 displays the boundary line display image 129 on the display 15. As shown in FIG. 24, in a case where the boundary line display image 129 in which the set boundary line 18 is displayed on the tablet 17 is transmitted to the processor device 14, the boundary line display image 129 displayed in the selected still image region 96 of the tablet 17 is displayed in the fixed display still image region 83 of the display 15 in synchronization with the display of the tablet 17.

It is preferable that the display 15 comprises a main screen and a sub screen. For example, it is preferable that the video image 82a of the endoscopic image being examined is displayed in the live video region 82 (see FIG. 11) which is the main screen, and the boundary line display image 129 is displayed in the fixed display still image region 83 (see FIG. 11) which is the sub screen. Further, two or more sub screens are provided, and the boundary line display image 129 is displayed in the fixed display still image region 83, which is one sub screen, and the still image 19 acquired as the temporary display still image region 81 (see FIG. 11) is displayed on the other sub screen. Therefore, the still image 19 appropriate for displaying the boundary line 18 can be easily and quickly selected, and the boundary line display image 129 in which the boundary line 18 is displayed after the still image 19 is selected can be observed while comparing the boundary line display image 129 with the endoscopic image being examined. The display device is not limited to the display 15, and the number of display devices is not limited to one or two. In some cases, the number of display devices, the screens to be displayed, or the like can be appropriately set.

The boundary line 18 may be displayed on the video image 82a so as to correspond to the boundary line 18 displayed on the boundary line display image 129. In a case where the boundary line 18 is displayed on the video image 82a, registration is performed between each frame of the video image 82a and the boundary line display image 129, and then the boundary line 18 is superimposed and displayed. A frame refers to an endoscopic image obtained through a single imaging. The video image 82a is, for example, 60 frames per second (fps).

It is preferable that the boundary line display image 129 is enlarged, reduced, or rotated in conformity with the frame of the video image 82a, and then the boundary line display image 129 is superimposed on the frame of the video image 82a. In addition, in a case where the boundary line display image 129 is an image obtained by imaging an observation target in a range larger than the frame of the video image 82a, that is, in a case where the frame of the video image 82a is included in the boundary line display image 129, the frame of the video image 82a may be superimposed and displayed on the boundary line display image 129. On the other hand, in a case where the boundary line display image 129 is an image obtained by imaging an observation target in a range smaller than the frame of the video image 82a, that is, in a case where the boundary line display image 129 is included in the frame of the video image 82a, the boundary line display image 129 may be superimposed and displayed on the frame of the video image 82a.

Whether or not to display the boundary line 18 on the video image 82a may be controlled based on the user's instruction or the endoscopic image. By freely controlling the display of the boundary line 18 on the video image 82a, it is possible to display the boundary line 18 on the video image 82a according to the user's desire. The display of the boundary line 18 may be controlled based on the endoscopic image. For example, in a case where it is determined that the endoscope is moving by analyzing the endoscopic image, a control can be performed such that the boundary line 18 is not automatically displayed, and in a case where a detailed observation is performed without moving the endoscope and the region of interest exists in the observation target, a control can be performed such that the boundary line 18 is automatically displayed or the like. As a result, the boundary line 18 is automatically displayed even without any instruction from the user, which may be advantageous.

By displaying the boundary line 18 on the video image 82a so as to correspond to the boundary line 18 displayed on the boundary line display image 129, an appropriately set boundary line 18 can be displayed on the video image 82a of the endoscopic examination. Therefore, this is a useful support in a case where a doctor needs to determine the boundary line 18 during the diagnosis, ESD, EMR, or the like.

The boundary line 18 to be displayed on the boundary line display image 129 is displayed by being updated for each setting of the boundary line 18. The setting is performed not only in a case of generating the boundary line 18 but also in a case of correcting the boundary line 18. Therefore, the medical image processing device can newly set the boundary line 18 obtained by correcting the boundary line 18 displayed on the boundary line display image 129, as the boundary line 18.

As described above, the medical image processing device is configured such that the boundary line display image 129 in which the boundary line 18 set in the still image 19 is displayed is generated, the boundary line display image 129 is displayed on the display 15 together with the video image 82a of the endoscopic image, which is the live video, and the boundary line 18 to be displayed is displayed by being updated for each setting of the boundary line 18. Therefore, a highly accurate boundary line 18 can be generated and displayed. In addition, since the boundary line 18 is set in the still image 19, the problem of the boundary line 18 changing for each frame and becoming cumbersome can be mitigated even in a case where the boundary line 18 is automatically generated and set. Further, since the still image 19 for which the boundary line 18 is displayed can be selected at any time, the boundary line 18 can be set in an appropriate still image 19 depending on the scene. Furthermore, since the setting is made each time the boundary line 18 is generated or corrected, and the boundary line 18 is updated and displayed on the boundary line display image 129 for each setting of the boundary line 18, a more appropriate boundary line 18 can be updated and displayed.

Figure 25:
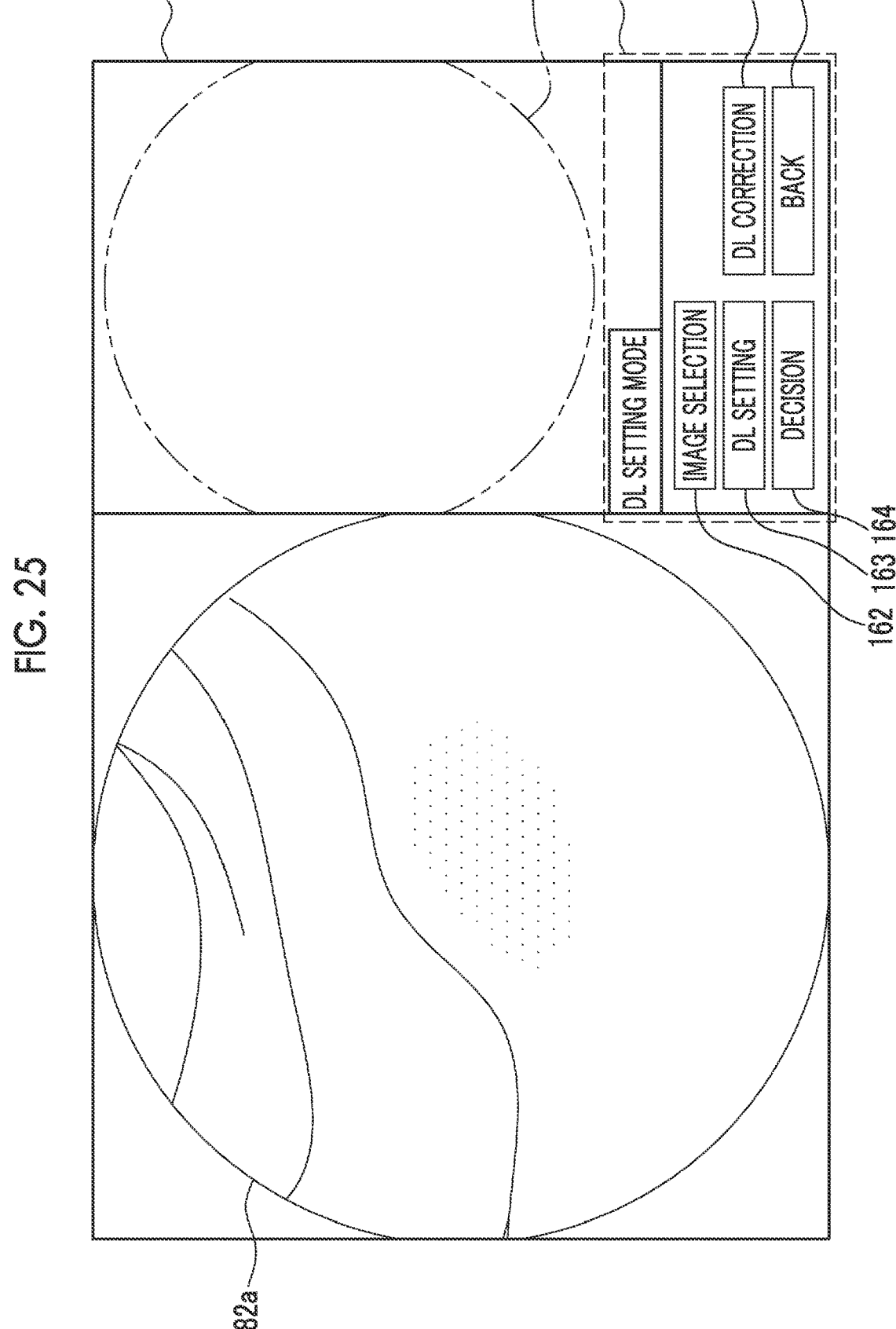
FIG. 25 is an image diagram of the display in a DL setting mode.

In a case where the boundary line 18 is generated without using the tablet 17, the generation can be performed as follows. During the examination, the still image 19 is acquired, and on the display 15, the video image 82a of the endoscopic image being examined is displayed in the live video region 82 (see FIG. 11). As shown in FIG. 25, an instruction to generate the boundary line 18 is issued through the keyboard 16, and a DL setting mode in which a boundary line setting screen 161 is displayed on the display 15 is set.

Figure 26:
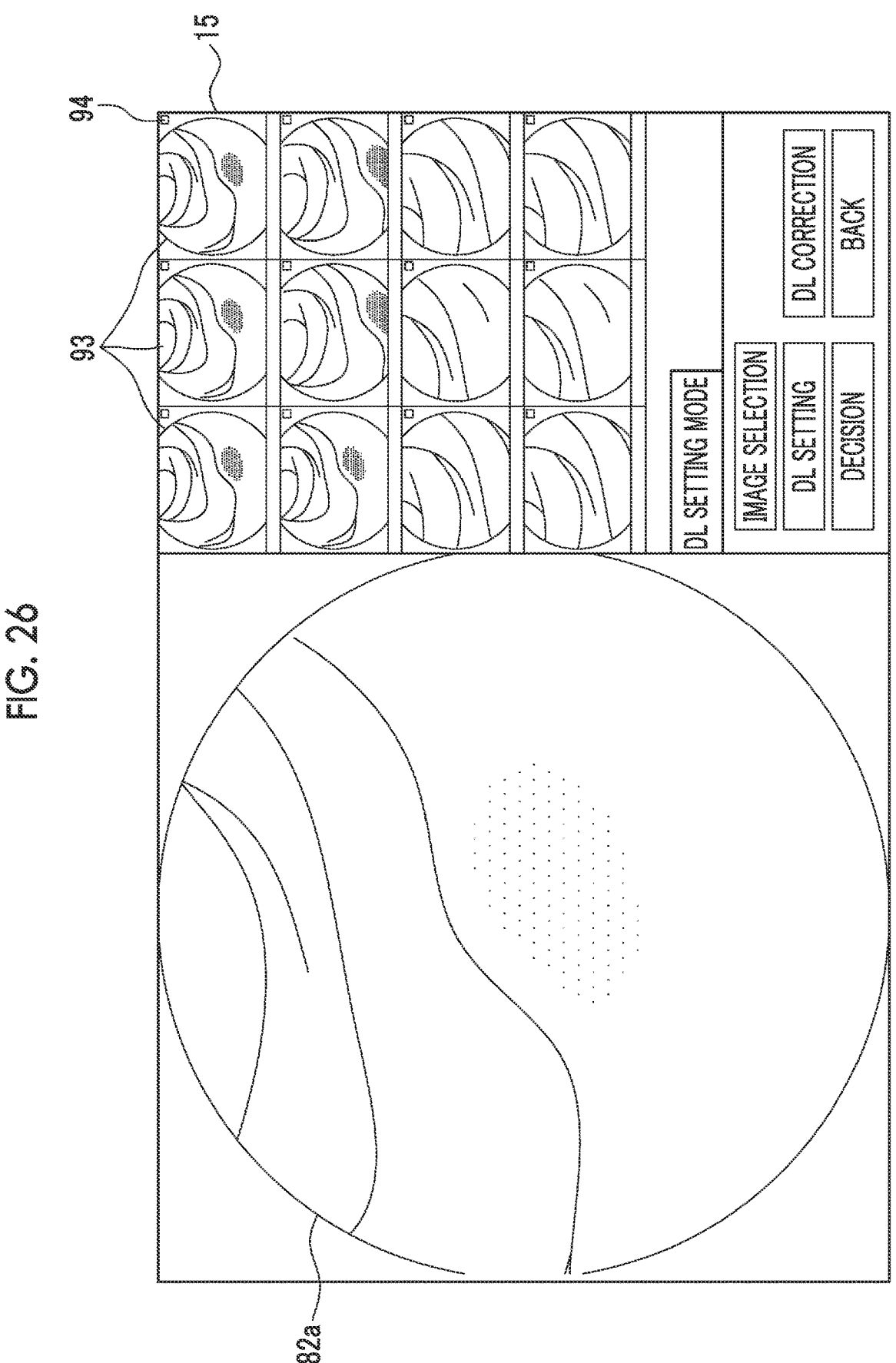
FIG. 26 is an image diagram of the display including the thumbnail.

As shown in FIG. 26, in a case where an image selection button 162 is pressed in the DL setting mode, thumbnails of the acquired still images 19 are displayed. The still image 19 for which the boundary line 18 is set is selected from the thumbnails with an arrow key of the keyboard 16 or the like. In a case where the still image 19 is selected, the selected still image 19 is displayed in the fixed display still image region 83. In a case where the boundary line 18 is set in the still image 19 displayed in the fixed display still image region 83, a DL setting button 163 is pressed. By pressing the DL setting button 163, the boundary line 18 is automatically generated. In a case of correcting the generated boundary line 18, a DL correction button 165 is pressed. The correction is the same as described above. In a case where the generation of the boundary line 18 is completed, a decision button is selected and pressed with the arrow key. After a decision button 164 is pressed, the boundary line 18 is set, and the boundary line display image 129, which is the still image 19 in which the boundary line 18 is set, is continuously displayed in the fixed display still image region 83. In a case where a back button 166 is pressed, the DL setting mode ends, and the screen returns to the home screen.

As described above, the generation, correction, setting, and the like of the boundary line 18 can be accurately and easily performed without using the tablet 17.

The boundary line 18 is updated and displayed for each setting of the boundary line 18, but the update of the boundary line 18 may be ended based on the user's instruction or the endoscopic image. In a case where no further update is required, such as a case where the boundary line 18 is fixed or a case where it is no longer necessary to display the boundary line 18, the update can be ended. As a result, in a case where an update is no longer required, it is possible to easily prevent the boundary line 18 from being continuously updated, so that it is possible to reduce the user's effort.

Figure 27:
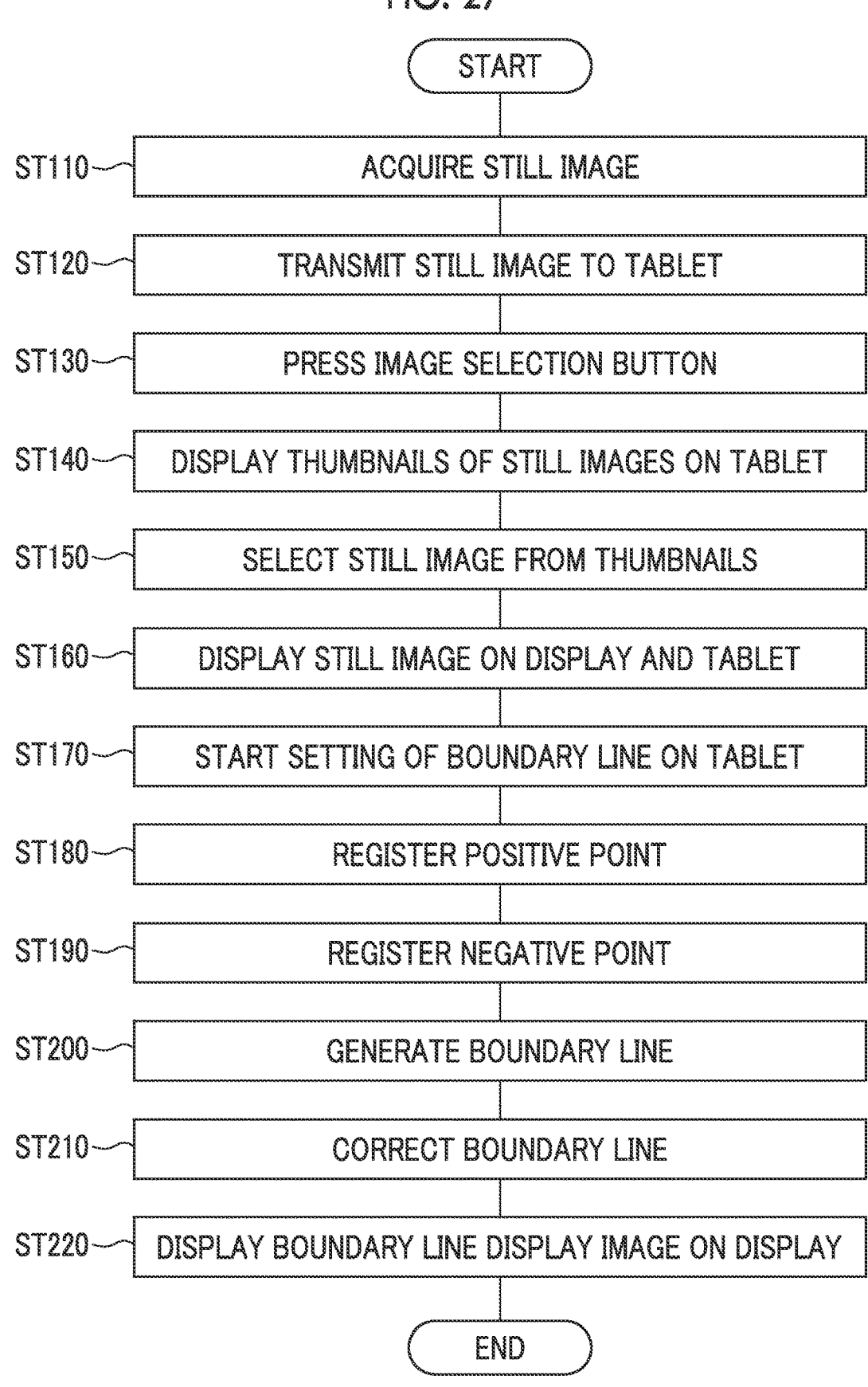
FIG. 27 is a flowchart illustrating a flow of boundary line setting by the medical image processing device.

A series of flows of endoscopic image processing of the present embodiment by the medical image processing device will be described with reference to a flowchart of FIG. 27. An endoscopic examination is started to acquire the still image 19 (step ST110). The acquired still image 19 is transmitted to the tablet 17 for each acquisition (step ST120). In a case where it is desired to display the latest three still images 19 on the display 15, to continue the endoscopic examination while updating the display of the still images 19, and to set the boundary line 18, the image selection button 92a is pressed on the tablet 17 (step ST130). The thumbnails 93 of the still images 19 are displayed on the tablet 17 (step ST140). In the tablet 17, the still image 19 for which the boundary line 18 is desired to be set is selected from the thumbnails 93 (step ST150). The selected still image 19 is displayed in the fixed display still image region 83 of the display 15 and displayed in the selected still image region 96 of the tablet 17 (step ST160). In the tablet 17, the DL setting button 92*b* is pressed to start the setting of the boundary line 18 (step ST170). In the tablet 17, the positive point selection button 122 is pressed to draw the positive point 127 on the selected still image 97, and the positive point registration button 122*a* is pressed to register the positive point 127 (step ST180). In the tablet 17, the negative point selection button 123 is pressed to draw the negative point on the selected still image 97, and the negative point registration button 123*a* is pressed to register the negative point 128 (step ST190). In a case where the registration of the positive point 127 and the negative point 128 is completed, the DL generation button 124 is pressed, and then the boundary line 18 is generated on the selected still image 97 (step ST200). The correction button 125 is pressed to correct the generated boundary line 18 (step ST210). In a case where the correction of the boundary line 18 is completed and the boundary line display image 129 is generated, the reflection-on-processor button 92*c* is pressed to display the boundary line display image 129 in the fixed display still image region 83 of the display 15 (step ST220).

In the above embodiment, the present invention is applied to a case where processing is performed on the endoscopic image, but the present invention can also be applied to a processor device, a medical image processing device, a medical image processing system, or the like that processes a medical image other than the endoscopic image.

Figures 28, 29:
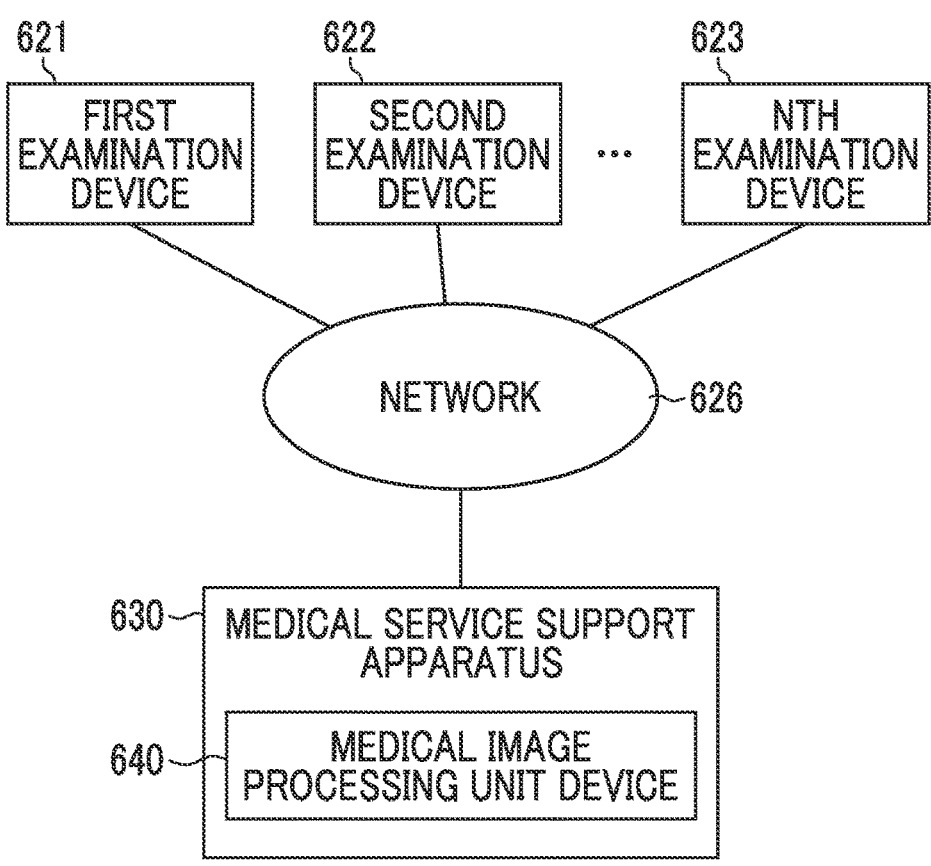
FIG. 28 is an explanatory diagram illustrating a case where the medical image processing device is provided in a diagnosis support apparatus.
FIG. 29 is an explanatory diagram illustrating a case where the medical image processing device is provided in a medical service support apparatus.

As shown in FIG. 28, some or all of the image processing unit 55 and/or the central control unit 58 in the endoscope system 10 can be provided in, for example, the diagnosis support apparatus 610 that acquires an image captured by the endoscope 12 directly from the endoscope system 10 or indirectly from a picture archiving and communication systems (PACS) 22. Similarly, some or all of a medical image processing unit device 640 which is a device that performs a function of a portion of the medical image processing device in the endoscope system 10 can be provided in, for example, the diagnosis support apparatus 610 that acquires an image captured by the endoscope 12 directly from the endoscope system 10 or indirectly from the picture archiving and communication systems (PACS) 22.

In addition, as shown in FIG. 29, a medical service support apparatus 630 connected to various examination devices including the endoscope system 10, such as a first examination device 621, a second examination device 622, . . . , and an Nth examination device 623, via a network 626 can be provided with some or all of the image processing unit 55 and/or the central control unit 58, or some or all of the medical image processing unit device 640 in the endoscope system 10.

In the above embodiment, the hardware structure of a processing unit that executes various kinds of processing, such as the central control unit 58, the image acquisition unit 51, the DSP 52, the noise reduction unit 53, the image processing unit 55, the display control unit 56, and the video signal generation unit 57, which are provided in the processor device 14, and the central control unit (not shown), which is provided in the tablet 17, is various processors to be described below. The various processors include a central processing unit (CPU) that is a general-purpose processor functioning as various processing units by executing software (programs), a programmable logic device (PLD) that is a processor of which a circuit configuration can be changed after manufacturing, such as a field programmable gate array (FPGA), a dedicated electrical circuit that is a processor having a circuit configuration exclusively designed to execute various types of processing, and the like.

One processing unit may be composed of one of these various processors or may be composed of a combination of two or more processors of the same type or different types (for example, a plurality of FPGAs or a combination of a CPU and an FPGA). Alternatively, a plurality of processing units may be composed of one processor. A first example in which a plurality of processing units are composed of one processor includes an aspect in which one or more CPUs and software are combined to constitute one processor and the processor functions as a plurality of processing units, as represented by a computer such as a client or a server. A second example of the configuration includes an aspect in which a processor that realizes all the functions of a system including a plurality of processing units with one integrated circuit (IC) chip is used, as represented by a system on chip (SoC). As described above, various processing units are composed of one or more of the above various processors, as the hardware structure.

Furthermore, as the hardware structure of the various processors, more specifically, an electrical circuit (circuitry) in which circuit elements, such as semiconductor elements, are combined is used.

EXPLANATION OF REFERENCES

10: endoscope system
12: endoscope
12*a*: insertion part
12*b*: operation part
12*c*: bending portion
12*d*: distal end portion
12*e*: angle knob
12*f*: zoom operation portion
12*g*: mode selector switch
12*h*: forceps port
12*i*: freeze switch
13: light source device
14: processor device
15: display
16: keyboard
17: tablet
18: boundary line
18*a*: lesion region
18*b*: non-lesion region
19: still image
20: light source unit
20*a*: V-LED
20*b*: B-LED
20*c*: G-LED
20*d*: R-LED
21: light source processor
22: PACS
30*a*: illumination optical system
30*b*: imaging optical system
41: light guide
42: illumination lens
43: objective lens
44: zoom lens
45: imaging sensor
46: CDS/AGC circuit
47: A/D converter
51: image acquisition unit

52: DSP
53: noise reduction unit
54: memory
55: image processing unit
56: display control unit
57: video signal generation unit
58: central control unit
61: normal image processing unit
62: special image processing unit
63: boundary line processing unit
71: still image storage unit
72: target image setting unit
73: boundary line generation unit
74: boundary line correction unit
75: boundary line setting unit
76: boundary line display unit
81: temporary display still image region
82: live video region
82*a*: video image
83: fixed display still image region
91: touch panel
92*a*, 162: image selection button
92*b*, 126, 163: DL setting button
92*c*: reflection-on-processor button
93: thumbnail
94: check box
95, 164: decision button
96: selected still image region
97: selected still image
98: touch pen
101: boundary line detection section
102: drawing detection section
103: positive point/negative point analysis section
111: learning model
122: positive point selection button
122*a*: positive point registration button
122*b*: deletion button
122*c*, 134, 166: back button
123: negative point selection button
123*a*: negative point registration button
124: DL generation button
125: correction button
127: positive point
128: negative point
129: boundary line display image
131: manual button
132: enlargement button
133: reduction button
141: vertex
142: anomaly degree determination section
151: region with anomaly degree 1
152: region with anomaly degree 3
161: boundary line setting screen
165: DL correction button
610: diagnosis support apparatus
621: first examination device
622: second examination device
623: Nth examination device
626: network
630: medical service support apparatus
640: medical image processing unit device
ST110 to ST220: step
What is claimed is:
1. A medical image processing device comprising:
one or more processors configured to:
    acquire an endoscopic image obtained by imaging a
      subject with an endoscope;

set a boundary line, which indicates a boundary
      between a region of interest and a region of disin-
      terest in the subject, in a still image of the endoscopic
      image;
    generate a boundary line display image in which the set
      boundary line is displayed on the still image; and
    perform a control of displaying a video image of the
      endoscopic image and the boundary line display
      image on a display device,
    wherein the boundary line to be displayed on the
      boundary line display image is displayed by being
      updated for each setting of the boundary line,
  the region of interest is a lesion region in the still image,
    and
  the region of disinterest is a non-lesion region in the still
    image,
  wherein the one or more processors are further configured
    to detect and set the boundary line by determining a
    plurality of anomaly degrees based on the still image,
    wherein the plurality of anomaly degrees indicates a
    difference related to a color, a shape, or a surface layer
    mucosal structure of the subject,
  wherein the plurality of anomaly degrees corresponds to
    a plurality of regions existing around the boundary line,
  in response to an anomaly degree of the plurality of
    anomaly degrees being designated by an operation
    performed on the display device, the boundary line is
    corrected into a region of the plurality of regions with
    the designated anomaly degree.
  2. The medical image processing device according to
claim 1,
  wherein the display device includes a first display device
    and a second display device,
  the one or more processors are configured to perform a
    control of displaying the still image and/or the bound-
    ary line display image on the first display device and/or
    the second display device, and
  the second display device is provided in a small terminal
    connected to the medical image processing device.
  3. The medical image processing device according to
claim 2,
  wherein the one or more processors are configured to, in
    a case of displaying the still image, set the boundary
    line based on a drawing generated by a user on the
    displayed still image.
  4. The medical image processing device according to
claim 3,
  wherein the drawing is subjected to smoothing process-
    ing.
  5. The medical image processing device according to
claim 3,
  wherein the drawing is a positive point generated in the
    region of interest of the still image through a determi-
    nation of the user.
  6. The medical image processing device according to
claim 3,
  wherein the drawing is a negative point generated in the
    region of disinterest of the still image through a deter-
    mination of the user.
  7. The medical image processing device according to
claim 3,
  wherein the one or more processors are configured to
    perform a control of displaying the still image on the
    second display device, and
  the drawing is the drawing generated on the still image
    displayed on the second display device.

8. The medical image processing device according to claim 2, wherein the one or more processors are configured to perform a control of displaying the boundary line display image on the second display device.

9. The medical image processing device according to claim 2, wherein the one or more processors are configured to perform a control of displaying the video image on a main screen of the first display device and displaying the boundary line display image on a sub screen of the first display device.

10. The medical image processing device according to claim 2, wherein the one or more processors are configured to perform a control of displaying the still image on a sub screen of the first display device.

11. The medical image processing device according to claim 1, wherein the one or more processors are configured to newly set the boundary line obtained by correcting the boundary line displayed on the boundary line display image as the boundary line.

12. The medical image processing device according to claim 1, wherein the one or more processors are configured to display the boundary line on the video image corresponding to the boundary line displayed on the boundary line display image.

13. The medical image processing device according to claim 12, wherein the one or more processors are configured to control whether or not to display the boundary line on the video image based on a user's instruction or the endoscopic image.

14. The medical image processing device according to claim 1, wherein the one or more processors are configured to end update of the boundary line based on a user's instruction or the endoscopic image.

15. The medical image processing device according to claim 1, wherein the still image is acquired in the same examination as the video image or is acquired in an examination different from the video image.

16. An endoscope system comprising:

an endoscope that images a subject;

a display device; and the medical image processing device according to claim 1.

17. The endoscope system according to claim 16, wherein the display device includes a first display device and a second display device.

18. An operation method of a medical image processing device, comprising:

a step of acquiring an endoscopic image obtained by imaging a subject with an endoscope;

a step of setting a boundary line, which indicates a boundary between a region of interest and a region of disinterest in the subject, in a still image of the endoscopic image;

a step of generating a boundary line display image in which the set boundary line is displayed on the still image; a step of performing a control of displaying a video image of the endoscopic image and the boundary line display image on a display device, wherein the boundary line to be displayed on the boundary line display image is displayed by being updated for each setting of the boundary line, the region of interest is a lesion region in the still image, and the region of disinterest is a non-lesion region in the still image; and a step of detecting and setting the boundary line by determining a plurality of anomaly degrees based on the still image, wherein the plurality of anomaly degrees indicates a difference related to a color, a shape, or a surface layer mucosal structure of the subject, wherein the plurality of anomaly degrees corresponds to a plurality of regions existing around the boundary line, in response to an anomaly degree of the plurality of anomaly degrees being designated by an operation performed on the display device, the boundary line is corrected into a region of the plurality of regions with the designated anomaly degree.

* * * * *